(12) United States Patent
Auvin et al.

(10) Patent No.: US 6,747,024 B1
(45) Date of Patent: Jun. 8, 2004

(54) HETEROCYCLIC COMPOUNDS AND THEIR USE AS MEDICINES

(75) Inventors: Serge Auvin, Mauchamps (FR); Pierre-Etienne Chabrier de Lassauniere, Paris (FR)

(73) Assignee: Societe de Conseils de Recherches et d'Applications Scientifiques (S.C.R.A.S.) (FR)

( * ) Notice: Subject to any disclaimer, the term of this patent is extended or adjusted under 35 U.S.C. 154(b) by 0 days.

(21) Appl. No.: 10/111,994

(22) PCT Filed: Nov. 3, 2000

(86) PCT No.: PCT/FR00/03067

§ 371 (c)(1),
(2), (4) Date: Apr. 30, 2002

(87) PCT Pub. No.: WO01/32654

PCT Pub. Date: May 10, 2001

(30) Foreign Application Priority Data

Nov. 5, 1999 (FR) .............................................. 99 13858
May 23, 2000 (FR) ............................................ 00 06535

(51) Int. Cl.⁷ .................... C07D 407/12; C07D 405/12; C07D 413/12; A61K 31/353; A61K 31/341
(52) U.S. Cl. ............................... 514/224.8; 514/226.2; 544/37; 544/38; 544/39
(58) Field of Search .............................. 544/37, 38, 39; 514/224.8, 226.2

(56) References Cited

U.S. PATENT DOCUMENTS 5,691,368 A   11/1997   Peet et al. ................... 514/376

FOREIGN PATENT DOCUMENTS

| EP | 0603873 | 6/1994 |
| EP | 0641800 | 3/1995 |
| EP | 0925786 | 6/1999 |
| WO | 9621655 | 7/1996 |
| WO | 9825899 | 6/1998 |

OTHER PUBLICATIONS

Isaka et al., CAPLUS Abstract 125:301007, 1996.*
Payard et al., CAPLUS Abstract 85:32768, 1976.*
Shirai et al., CAPLUS Abstract 74:13097, 1971.*
Peet, et al. "Hydroxyoxazolidines . . . Calpain", Bioorganic & Medicinal Chemistry Letters, GB, Oxford, vol. 9, No. 16, Aug. 16, 1999 pp. 2365–2370.

* cited by examiner

Primary Examiner—Deepak Rao
(74) Attorney, Agent, or Firm—Muserlian, Lucas and Mercanti

(57) ABSTRACT

The present invention relates to new heterocyclic derivatives having an inhibitory activity on calpains and/or a trapping activity on reactive oxygen species, of formula

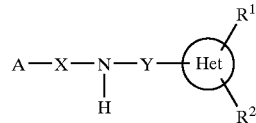

in which A, X, Y, R1, $R^2$ and Het represent variable groups.

The invention also relates to their preparation methods, the pharmaceutical preparations containing them and their use for therapeutic purposes, in particular as inhibitors of calpains and/or traps of reactive oxygen species, selectively or non-selectively.

17 Claims, No Drawings

HETEROCYCLIC COMPOUNDS AND THEIR USE AS MEDICINES

This application is a 371 PCT/FR00/03067 filed Nov. 3, 2000.

The present invention relates to new heterocyclic derivatives having an inhibitory activity on calpains and/or a trapping activity on reactive oxygen species (ROS's). The invention also relates to methods for their preparation, pharmaceutical preparations containing them and their use for therapeutic purposes, in particular as inhibitors of calpains and selective or non-selective ROS traps.

Given the potential role of calpains and ROS's in physiopathology, the new derivatives according to the invention can produce beneficial or favourable effects in the treatment of pathologies involving these enzymes and/or these radicular species, and in particular:

- inflammatory and immunological diseases such as for example rheumatoid arthritis, pancreatitis, multiple sclerosis, inflammation of the gastro-intestinal tract (ulcerative or non-ulcerative colitis, Crohn's disease),
- cardiovascular and cerebrovascular diseases including for example arterial hypertension, septic shock, cardiac or cerebral infarctions of ischemnic or hemorrhagic origin, ischemia as well as disorders linked to platelet aggregation,
- disorders of the central or peripheral nervous system such as for example neurodegenerative diseases where there can in particular be mentioned trauma to the brain or spinal cord, sub-arachnoid haemorrhages, epilepsy, ageing, senile dementia, including Alzheimer's disease, Huntington's chorea, Parkinson's disease, peripheral neuropathies,
- osteoporosis,
- muscular dystrophies,
- proliferative diseases such as for example atherosclerosis or recurrence of stenosis,
- cataracts,
- organ transplants,
- auto-immune and viral diseases such as for example lupus, AIDS, parasitic and viral infections, diabetes and its complications, multiple sclerosis,
- cancer,
- all the pathologies characterized by an excessive production of ROS's and/or activation of calpains.

In all these pathologies, there is experimental evidence demonstrating the involvement of ROS's (Free Radic. Biol. Med. (1996) 20, 675–705; Antioxid. Health. Dis. (1997) 4 (Handbook of Synthetic Antioxidants), 1–52) as well as the involvement of calpains (Trends Pharmacol. Sci. (1994) 15, 412419; Drug News Perspect (1999) 12, 73–82). For example, cerebral lesions associated with cerebral infarction or experimental cranial trauma are reduced by antioxidants (Acta Physiol. Scand. (1994) 152, 349–350; 1. Cereb. Blood Flow Metabol. (1995) 15, 948–952; J Pharmacol Exp Ther (1997) 2, 895–904) as well as by inhibitors of calpains (Proc Natl Acad Sci USA (1996) 93, 3428–33; Stroke, (1998) 29, 152–158; Stroke (1994) 25, 2265–2270).

A subject of the present invention is therefore compounds of general formula (I)

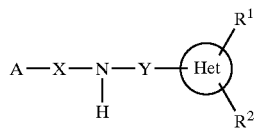

(I)

in which
$R^1$ represents a hydrogen atom, an —$OR^3$, —$SR^3$, oxo or cyclic acetal radical,
  in which $R^3$ represents a hydrogen atom, an alkyl, arylalkyl, heterocycloalkylcarbonyl, alkylcarbonyl, arylcarbonyl or aralkylcarbonyl radical,
  in which the alkyl, aryl or heterocycloalkyl radicals are optionally substituted by one or more identical or different substituents chosen from: alkyl, OH, alkoxy, nitro, cyano, halogen or —$NR^4R^5$;
  $R^4$ and $R^5$ represent, independently, a hydrogen atom or an alkyl radical, or $R^4$ and $R^5$ together with the nitrogen atom to which they are attached form an optionally substituted heterocycle,
$R^2$ represents a hydrogen atom, an alkyl, aryl or aralkyl radical, the aryl group being optionally substituted by one or more identical or different radicals chosen from: —$OR^6$, —$NR^7R^8$, halogen, cyano, nitro or alkyl,
  in which $R^6$, $R^7$ and $R^8$ represent, independently, a hydrogen atom, an alkyl, aryl, aralkyl, alkylcarbonyl, arylcarbonyl or aralkylcarbonyl radical;
A represents
  either an A1 or A'1 radical

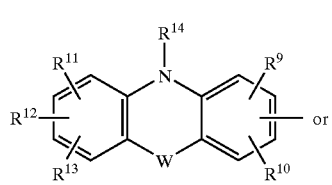

A1

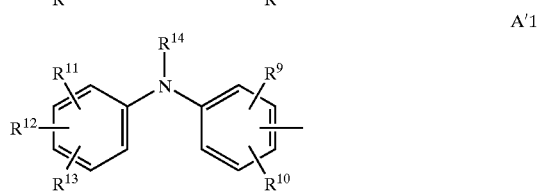

A'1 in which $R^9$, $R^{10}$, $R^{11}$, $R^{12}$, $R^{13}$ represent, independently, a hydrogen atom, a halogen, the OH group, an alkyl, alkoxy, cyano, nitro or —$NR^{15}R^{16}$ radical,
$R^{15}$ and $R^{16}$ represent, independently, a hydrogen atom, an alkyl radical or a —$COR^{17}$ group, or $R^{15}$ and $R^{16}$ together with the nitrogen atom to which they are attached form an optionally substituted heterocycle,
$R^{17}$ represents a hydrogen atom, an alkyl, alkoxy or —$NR^{18}R^{19}$ radical,
$R^{18}$ and $R^{19}$ represent, independently, a hydrogen atom or an alkyl radical, or $R^{18}$ and $R^{19}$ together with the nitrogen atom to which they are attached form an optionally substituted heterocycle,
$R^{14}$ represents a hydrogen atom, an alkyl radical or a —$COR^{20}$ group,
$R^{20}$ represents a hydrogen atom, an alkyl, alkoxy, aryl, aralkyl, heterocycloalkyl or —$NR^{21}R^{22}$ radical,
  in which the alkyl, aryl or heterocycloalkyl radicals are optionally substituted by one or more identical or different substituents chosen from: alkyl, OH, alkoxy, nitro, cyano, halogen or —NR$^4$R$^5$;

R$^{21}$ and R$^{22}$ represent, independently, a hydrogen atom or an alkyl radical, or R$^{21}$ and R$^{22}$ together with the nitrogen atom to which they are, attached form an optionally substituted heterocycle, W represents a bond, O or S or also an —NR$^{23}$ radical, in which R$^{23}$ represents a hydrogen atom or an alkyl radical;

or an A2 radical

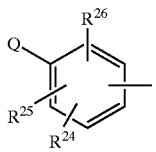

A2 in which

R$^{24}$, R$^{25}$ and R$^{26}$ represent, independently, a hydrogen, a halogen, the OH or SR$^{27}$ group, an alkyl, alkenyl, alkoxy radical or an —NR$^{28}$R$^{29}$ radical, R$^{27}$ represents a hydrogen atom or an alkyl radical, R$^{28}$ and R$^{29}$ represent, independently, a hydrogen atom, an alkyl radical or a —COR$^{30}$ group, or R$^{28}$ and R$^{29}$ form together with the nitrogen atom to which they are attached an optionally substituted heterocycle, R$^{30}$ represents a hydrogen atom, an alkyl, alkoxy or —NR$^{31}$R$^{32}$ radical, R$^{31}$ and R$^{32}$ represent, independently, a hydrogen atom or an alkyl radical, or R$^{31}$ and R$^{32}$ together with the nitrogen atom to which they are attached form an optionally substituted heterocycle, Q represents —OR$^{33}$, —SR$^{33}$, —NR$^{34}$R$^{35}$ or an aryl radical substituted by one or more identical or different substituents chosen from: halogen, the OH group, an alkyl, alkoxy, cyano, nitro or —NR$^{15}$R$^{16}$ radical, R$^{33}$ represents a hydrogen atom, an alkyl, arylalkyl, heterocycloalkylcarbonyl, alkylcarbonyl, arylcarbonyl or aralkylcarbonyl radical,
  in which the alkyl, aryl or heterocycloalkyl radicals are optionally substituted by one or more identical or different substituents chosen from: alkyl, OH, alkoxy, nitro, cyano, halogen or —NR$^4$R$^5$;

R$^{34}$ and R$^{35}$ represent, independently, a hydrogen atom, an alkyl radical or a —CO—R$^{36}$ radical, or together with the nitrogen atom to which they are attached form an optionally substituted heterocycle, R$^{36}$ representing an alkyl radical;

or an A3 radical

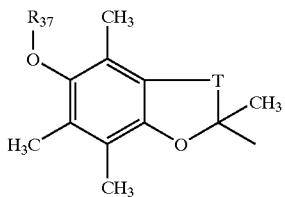

A3 in which R$^{37}$ represents a hydrogen atom, an alkyl, arylalkyl, heterocycloalkylcarbonyl, alkylcarbonyl, arylcarbonyl or aralkylcarbonyl radical,
  in which the alkyl, aryl or heterocycloalkyl radicals are optionally substituted by one or more identical or different substituents chosen from: alkyl, OH, alkoxy, nitro, cyano, halogen or —NR$^4$R$^5$;

T represents a —(CH$_2$)$_m$— radical with m=1 or 2;

or an A4 radical

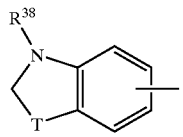

A4 in which R$^{38}$ represents a hydrogen atom, an alkyl, —(CH$_2$)$_q$—NR$^{39}$R$^{40}$ or aralkyl radical, the aryl group being optionally substituted by one or more identical or different substituents chosen from: OH, alkyl, halogen, nitro, alkoxy or —NR$^{39}$R$^{40}$, q being an integer comprised between 2 and 6;

or an A5 radical

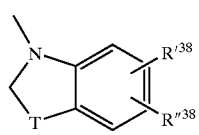

A5 in which R'$^{38}$ and R"$^{38}$ represent independently a hydrogen atom, nitro, —NR'$^{39}$R'$^{40}$, an alkyl or arylalkyl radical, the aryl group being optionally substituted by one or more identical or different substituents chosen from: OH, the alkyl, halogen, nitro, alkoxy or —NR$^{39}$R$^{40}$ radicals, R'$^{39}$, R'$^{40}$, R$^{39}$ and R$^{40}$ represent, independently, a hydrogen atom, an alkyl radical or a —COR$^{41}$ group, or R$^{39}$ and R$^{40}$ or R'$^{39}$ and R'$^{40}$ together with the nitrogen atom form an optionally substituted heterocycle, R$^{41}$ represents a hydrogen atom, an alkyl, alkoxy or —NR$^{42}$R$^{43}$ radical, R$^{42}$ and R$^{43}$ represent, independently, a hydrogen atom or an alkyl radical, or R$^{42}$ and R$^{43}$ together with the nitrogen atom to which they are attached form an optionally substituted heterocycle, T representing a —(CH$_2$)$_m$— radical with m=1 or 2, or finally an A6 radical

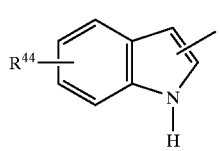

A6 in which R$^{44}$ represents a hydrogen atom, the OH group or an alkyl or alkoxy radical;

X represents —(CH$_2$)$_n$—, —(CH$_2$)$_n$—CO—, —N(R$^{45}$)—CO—(CH$_2$)$_n$—CO—, —N(R$^{45}$)—CO—D—CO—, —CO—N(R$^{45}$)—D—CO—, —CO—D—CO—, —CH=CH—(CH$_n$)$_2$—CO—, —N($^{45}$)—(CH$_2$)$_n$—CO—, —N(R$^{45}$)—CO—C(R$^{46}$R$^{47}$)—CO—, —O—(CH$_2$)$_n$—CO—, —N(R45)—CO—NH—C(R$^{46}$R$^{47}$)—CO—, —CO—N(R$^{45}$)—C(R$^{46}$R$^{47}$)—CO—, —S—(CH$_2$)$_n$—CO— or —Z—CO—;

D represents a phenylene radical optionally substituted by one or more identical or different radicals chosen from alkyl, alkoxy, OH, nitro, halogen, cyano, or carboxyl optionally esterified by an alkyl radical;

Z represents a heterocycle, $R^{45}$ represents a hydrogen atom or an alkyl radical, $R^{46}$ and $R^{47}$ represent, independently, a hydrogen atom, an alkyl, aryl or aralkyl radical the alkyl and aryl groups of which are optionally substituted by one or more identical or different substituents chosen from: the OH, —SH, halogen, nitro, alkyl, alkoxy, alkylthio, aralkoxy, aryl-alkylthio, —NR$^{48}$R$^{49}$ and carboxyl group optionally esterified by an alkyl radical;

$R^{48}$ and $R^{49}$ represent, independently, a hydrogen atom, an alkyl radical or a —COR$^{50}$ group, or $R^{48}$ and $R^{49}$ together with the nitrogen atom to which they are attached form an optionally substituted heterocycle, $R^{50}$ represents a hydrogen atom, an alkyl, alkoxy or —NR$^{51}$R$^{52}$ radical, $R^{51}$ and $R^{52}$ represent, independently, a hydrogen atom or an alkyl radical, or $R^{51}$ and $R^{52}$ together with the nitrogen atom to which they are attached, form an optionally substituted heterocycle;

n being an integer comprised between 0 and 6;

Y represents —(CH$_2$)$_p$—, —C(R$^{53}$R$^{54}$)—(CH$_2$)$_p$—, —C(R$^{53}$R$^{54}$)—CO—;

$R^{53}$ and $R^{54}$ represent, independently, a hydrogen atom, an alkyl radical, an aralkyl radical the aryl group of which is optionally substituted by one or more identical or different substituents chosen from: the OH, halogen, nitro, alkyl, alkoxy, —NR$^{55}$R$^{56}$ group, $R^{55}$ and $R^{56}$ represent, independently, a hydrogen atom, an alkyl radical or a —COR$^{57}$ group, or $R^{55}$ and $R^{56}$ together with the nitrogen atom to which they are attached, form an optionally substituted heterocycle, $R^{57}$ represents a hydrogen atom, an alkyl, alkoxy or —NR$^{58}$R$^{59}$ radical, $R^{58}$ and $R^{59}$ represent, independently, a hydrogen atom or an alkyl radical, or $R^{58}$ and $R^{59}$ together with the nitrogen atom to which they are attached form an optionally substituted heterocycle;

p being an integer comprised between 0 and 6;

Het represents a heterocycle, as well as the addition salts with mineral and organic acids or with mineral and organic bases of said compounds of general formula (I), with the exception of the compounds of formula (I) in which when Het represents tetrahydrofuran or tetrahydropyran, $R^1$ represents the OR$^3$ radical with $R^3$ representing a hydrogen atom, an alkyl, arylalkyl, heterocycloalkylcarbonyl radical the heterocycloalkyl radical of which is connected by a carbon atom, alkylcarbonyl, arylcarbonyl or aralkylcarbonyl radical, $R^2$ represents a hydrogen and Y represents the —(CH$_2$)$_p$—radical with p=0, then X does not represent —CO—N(R$^{45}$)—C(R$^{46}$R$^{47}$)—CO— with R$^{45}$=R$^{46}$=H.

In certain cases, the compounds according to the present invention can comprise asymmetrical carbon atoms (of "R" or "S" configuration). As a result, the present invention includes the enantiomeric, diastereoisomeric forms and all combinations of these forms, including the "RS" racemic mixtures. In an effort to simplify matters, when no specific configuration is indicated in the structural formulae, it should be understood that the two enantiomeric (or diastereoisomeric) forms and their mixtures are represented.

By alkyl, unless specified otherwise, is meant a linear or branched alkyl radical containing 1 to 6 carbon atoms such as, for example, the methyl, ethyl, propyl, isopropyl, butyl, isobutyl, sec-butyl and tert-butyl, pentyl, neopentyl, isopentyl, hexyl, isohexyl radicals. The alkoxy radicals can correspond to the alkyl radicals indicated above such as for example the methoxy, ethoxy, propyloxy or isopropyloxy radicals but also linear, secondary or tertiary butoxy. Similarly the alkylthio radicals can correspond to the alkyl radicals indicated above such as for example methylthio or ethylthio.

By alkenyl, unless otherwise specified, is meant a linear or branched alkyl radical containing 1 to 6 carbon atoms and having at least one unsaturation (double bond). By halogen, is meant the fluorine, chlorine, bromine or iodine atoms.

By aryl, is meant a carbocyclic or heterocyclic system comprising at least one aromatic ring, a system being called heterocyclic when at least one of the rings composing it comprises a heteroatom (O, N or S). As an example of a carbocyclic aryl radical, there can be mentioned phenyl or naphthyl. As an example of a heterocyclic aryl radical (or heteroaryl), there can be mentioned thienyl, furyl, pyrrolyl, imidazolyl, pyrazolyl, isothiazolyl, thiazolyl, isoxazolyl, oxazolyl, pyridyl, pyrazinyl, pyrimidyl, benzothienyl, benzofuryl and indolyl.

The term heterocycle (or heterocycloalkyl), represented for example by the Het or Z radicals, preferably represents a saturated or unsaturated, mono or bicyclic heterocycle, comprising 1 to 5 heteroatoms chosen from O, S, N. The nitrogen atom can optionally be substituted by a radical chosen from: alkyl, aryl, aralkyl and alkylcarbonyl. As an example of a saturated heterocycle, there can be mentioned tetrahydrofuran, tetrahydropyran, oxetane, oxepane, tetrahydrothiophene, tetrahydrothiopyran, thietane, pyrrolidine, piperidine, azetidine, 1,3-dioxane, 1,3-dioxolane, 1,3-dithiolane, 1,3-dithiane, 1,3-oxathiolane, 1,3-oxazolidine, 1,3-imidazolidine or 1,3-thiazolidine. As an example of an unsaturated heterocycle, there can be mentioned: thiophene, furan, pyrrol, imidazole, pyrazole, isothiazole, thiazole, isoxazole, oxazole, pyridine, pyrazine, pyrimidine, benzimidazole, benzofun, benzopyran, 1,3-benzothiazole, benzoxazole, quinoline.

The arylalkyl (or aralkyl) radicals designate the radicals in which the aryl and alkyl radicals respectively are as defined above such as for example benzyl, phenylethyl or naphthylmethyl. The aralkoxy (aryl-alkoxy) radicals designate the radicals in which the aryl and alkoxy radicals respectively are as defined above such as for example benzyloxy or phenylethoxy. The arylalkylthio radicals designate the radicals in which the aryl and alkylthio radicals respectively are as defined above such as for example benzylthio.

The alkylcarbonyl, heterocycloalkylcarbonyl, arylcarbonyl or aralkylcarbonyl radicals designate the radicals in which the alkyl, heterocycloalkyl, aryl and aralkyl radicals respectively have the meaning indicated previously.

In the case of radicals of formula —NR$^i$R$^j$ where R$^i$ and R$^j$ together with the nitrogen atom to which they are attached form an optionally substituted heterocycle, the heterocycle is preferably saturated and comprises 4 to 7 members and 1 to 3 heteroatoms including the nitrogen atom already present, the additional heteroatoms being chosen independently from the group constituted by the O, N and S atoms. Said heterocycle can be, for example, the azetidine, pyrrolidine, piperidine, piperazine, morpholine or thiomorpholine ring. Said heterocycle can be substituted by one or more identical or different substituents chosen from the hydroxy group, an alkyl, aryl, aralkyl or alkoxy radical or a halogen atom.

A more particular subject of the invention is the compounds of formula (I) as defined above, in which Het represents a monocyclic radical containing 1 to 2 heteroatoms chosen from O and N, and preferably a radical corresponding to the tetrahydrofuran, dioxolane, pyrrolidine, 1,3-oxazolidine ring, and $R^1$ represents the hydrogen atom, the —$OR^3$ or oxo radical.

A more particular subject of the invention is the compounds of formula (I) as defined above, in which X represents —$(CH_2)_n$—, —$(CH_2)_n$—CO—, —O—$(CH_2)_n$—CO—, —CO—$N(R^{45})$—D—CO—, —$N(R^{45})$—CO—$(CH_2)_n$—CO—, —$N(R^{45})$—CO—$C(R^{46}R^{47})$—CO—, —$N(R^{45})$—CO—NH—$C(R^{46}R^{47})$—CO—, —$N(R^{45})$—$(CH_2)_n$—CO—, —CO—$N(R^{45})$—$C(R^{46}R^{47})$—CO— or —Z—CO—, and preferentially when $R^{45}$ and $R^{47}$ represent the hydrogen atom, $R^{46}$ represents the hydrogen atom, an alkyl or phenyl radical, D represents the phenylene radical and Z represents the thiazole radical.

A more particular subject of the invention is also compounds of formula (I) as defined above, in which $R^2$ represents a hydrogen atom or an aralkyl radical, and preferably the benzyl radical.

A more particular subject of the invention is also compounds of formula (I) as defined above, in which A represents
either A1 with W representing the sulphur atom,
or A'1
or A2 with $R^{24}$, $R^{25}$ and $R^{26}$ which represent, independently, a hydrogen or an alkyl radical and Q which represents —$OR^{33}$,
or A3 with T representing the —$(CH_2)_2$—radical;
or A4 with T representing the —$(CH_2)$—radical,
and preferably the radicals of formula

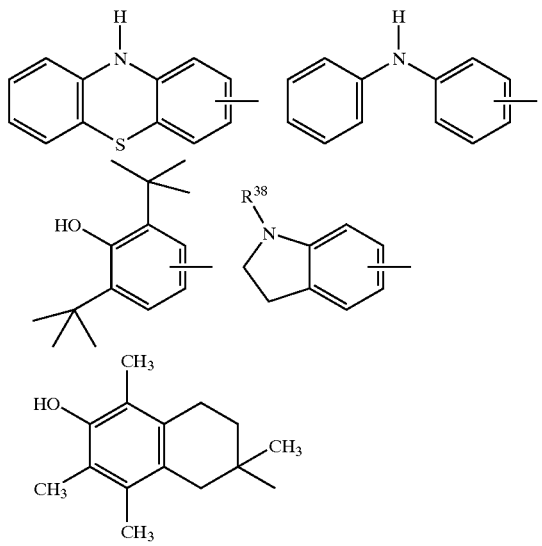

A more particular subject of the invention is also the compounds described hereafter in the examples and preferably the products corresponding to the following formulae:

(2R)-6-hydroxy-N-[(3S)-2-hydroxytetrahydro-3-furayl]-2,5,7,8-tetramethyl-3,4-dihydro-2H-chromene-2-carboxamide;

N-1-(4-anilinophenyl)-N-4-[(3S)-2-hydroxytetrahydro-3-furanyl]succinamide;

(3S)-3-{[4-(4-anilinoanilino)-4-oxobutanoyl]amino}tetrahydro-2-furanyl acetate;

N-1-(4-anilinophenyl)-N-4-[(1S)-1-(1,3-dioxolan-2-yl)-3-methylbutyl]succinamide;

N-1-(4-anilinophenyl)-N-3-[(3S)-2-hydroxytetrahydro-3-furanyl]-2-phenylmalonamide;

3-(4-anilinoanilino)tetrahydro-2-furanol;

N-[(1S)-1-({[(3S)-2-hydroxytetrahydro-3-furanyl]amino}carbonyl)-3-methylbutyl]-10H-phenothiazine-2-carboxamide;

(3S)-3-({(2S)-4-methyl-2-[(10H-phenothiazin-2-ylcarbonyl)-amino]pentanoyl}amino)tetrahydro-2-furanyl acetate;

N-[(3S)-2-hydroxytetrahydro-3-furanyl]-2-(10H-phenothiazin-2-yl)-1,3-thiazol-4-carboxamide;

N-[4-({[(3S)-2-hydroxytetrahydro-3-furanyl]amino}carbonyl)phenyl]-10H-phenothiazine-2-carboxamide;

N-[(1S)-1-({[(3S)-2-hydroxytetrahydro-3-furanyl]amino}carbonyl)-3-methylbutyl]-10H-phenothiazine-1-carboxamide;

(3S)-3-({(2S)-4-methyl-2-[(10H-phenothiazin-2-ylcarbonyl)amino]pentanoyl}amino)tetrahydro-2-furanyl pivalate;

(3S)-3-({(2S)-4-methyl-2-[(10H-phenothiazin-2-ylcarbonyl)amino]pentanoyl}amino)-tetrahydro-2-furanyl3,3dimethylbutanoate;

(3S)-3-({(2S)-4-methyl-2-[(10H-phenothiazin-2-ylcarbonyl)amino]pentanoyl}amino)tetrahydro-2-furanyl benzoate;

(3S)-3-({(2S)-4-methyl-2-[(10H-phenothiazin-2-ylcarbonyl)amino]pentanoyl}amino)tetrahydro-2-furanyl phenylacetate;

(3S)-3-({(2S)-4-methyl-2-[(10H-phenothiazin-2-ylcarbonyl)amino]pentanoyl}amino)tetrahydro-2-furanyl (2S)-2-(dimethylamino)-3-phenylpropanoate;

(3S)-3-({(2S)-4-methyl-2-[(10H-phenothiazin-2-ylcarbonyl)amino]pentanoyl}amino)tetrahydro-2-furanyl 4-morpholinecarboxylate;

N-{(1S)-3-methyl-1-[(3-oxo-1-pyrrolidinyl)carbonyl]butyl}-10H-phenothiazine-2-carboxanmide;

2-(3,5-di-tert-butyl-4-hydroxyphenoxy)-N-[(3S)-2-hydroxytetrahydro-3-furanyl]acetamide;

$N^1$-[(3S)-2-hydroxytetrahydro-3-furanyl]-2-phenyl-$N^3$-(1-propyl-2,3-dihydro-1H-indol-5-yl)malonamide;

N-(2-anilinophenyl)-N'-[(3S)-2-hydroxytetrahydro-3-furanyl]urea;

N'-[(3S)-2-hydroxytetrahydro-3-furanyl]-$N^2$-(1-propyl-2,3-dihydro-1H-indol-5-yl)ethanediamnide;

(2R)-N-[(1S)-1-(1,3-dioxolan-2-yl)-2-phenylethyl]-6-hydroxy-2,5,7,8-tetramethyl-3,4-dihydro-2H-chromene-2-carboxamide;

N-[(3S)-2-hydroxytetrahydro-3-furanyl]-5-indolinecarboxamide.

The compounds of formula I according to the invention can be prepared via several synthesis routes according to the definition of the variable groups.

The compounds of general formula (I) in which Het represents the tetrahydrofuran ring and Y represents the —$(CH_2)_p$ radical, can be prepared according to the following diagram:

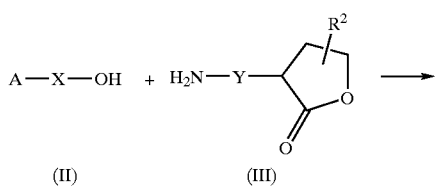

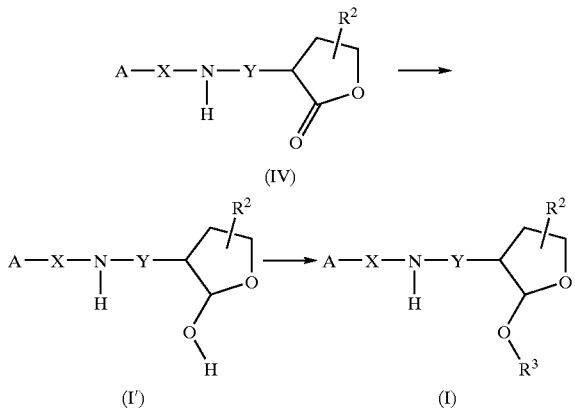

(IV)

(I')      (I)

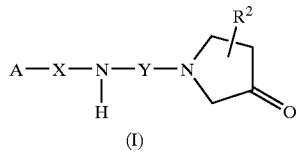

(I)

in which A, X, $R^2$ and $R^3$ are as described above, by condensation of the acids of general formula (II) on the amines of general formula(III), under standard conditions for peptide synthesis (M. Bodanszky and A. Bodanszky, The Practice of Peptide Synthesis, 145 (Springer-Verlag, 1984)) in THF, dichloromethane or DMF in the presence of a coupling reagent such as dicyclohexylcarbodiimide (DCC), 1,1'-carbonyldiimidazole (CDI) (J. Med. Chem. (1992), 35 (23), 4464–4472) or 1-(3-dimethylaminopropyl)-3-ethylcarbodiimide hydrochloride (EDC or WSCI) (John Jones, The chemical synthesis of peptides, 54 (Clarendon Press, Oxford, 1991)) in order to produce the intermediate carboxamides of general formula (IV). The lactonic ring of the intermediates of general formula (IV) is then reduced using a reducing agent such as, for example, diisobutylaluminium hydride (DIBAL), in an inert solvent such as, for example, THF or $CH_2Cl_2$, at a temperature varying from 0 to −78° C. The lactol derivative of general formula (I') obtained in this 1 s way can be acylated using, for example, an acid chloride ($R^3$—Cl) or an acid anhydride (acetic anhydride, benzoyl chloride, etc.) in the presence of a base such as, for example, triethylamine, in an inert solvent such as for example $CH_2Cl_2$ in order to produce the compound of general formula (I).

The compounds of formula (I) in which Het represents the pyrrolidinyl radical and Y represents —C($R^{53}R^{54}$)—CO—, $R^{53}$ and $R^{54}$ being as defined above, can be prepared according to the following diagram:

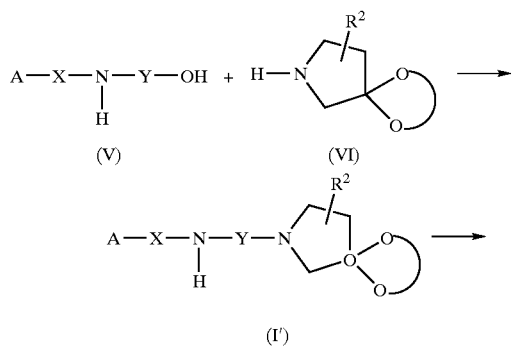

in which A, X and $R^2$ are as described above, by condensation of the acids of general formula (V) on the amines of general formula (VI) (J. Med. Chem. (1992) 35 (8), 1392–1398) under standard conditions for peptide synthesis, as described previously, in order to produce the compounds of general formula (I'). The optional deprotection of the ketone function is then carried out according to the methods described in the literature (T. W. Greene and P. G. M. Wuts, Protective Groups in Organic Synthesis, Second edition (Wiley-Interscience, 1991)), in order to produce the compounds of general formula (I).

The compounds of formula (I) in which Het represents the 1,3-dioxolane, 1,3-dioxane, 1,3-dithiane, 1,3-dithiolane, 1,3-oxathiolane, 1,3-oxazolidine, 1,3-imidazolidine or 1,3-thiazolidine ring, and Y represents —C($R^{53}R^{54}$)—CO—, $R^{53}$ and $R^{54}$ being as defined above, can be prepared according to the following diagram:

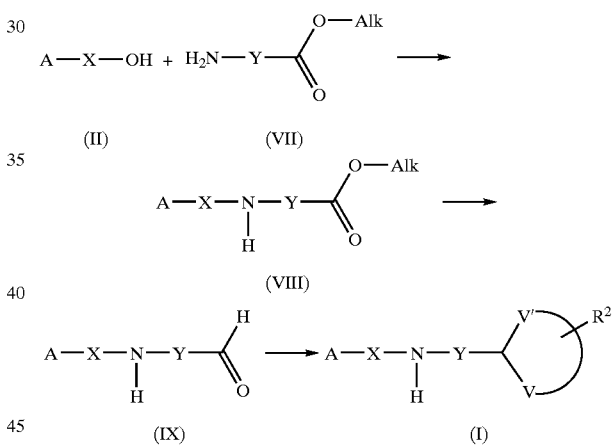

in which A, X and $R^2$ are as described above and V and V' represent independently N, O or S, by condensation of the acids of general formula (II) described previously, on the commercial amino-esters of general formula (VII), under the standard conditions for peptide synthesis described previously, in order to produce the intermediates of general formula (VIII). Reduction of the carboxylic ester using a reducing agent such as, for example, DIBAL, in an inert solvent such as, for example, THF or $CH_2Cl_2$, at a temperature varying from 0 to −78° C., leads to the aldehydes of general formula (IX). Conversion of the aldehyde to a heterocycle is carried out according to the methods in the literature (T. W. Greene and P. G. M. Wuts, Protective Groups in Organic Synthesis, Second edition (Wiley-Interscience, 1991)).

The compounds of formula (I) in which Het represents the oxazolidine ring can be prepared according to the following diagram:

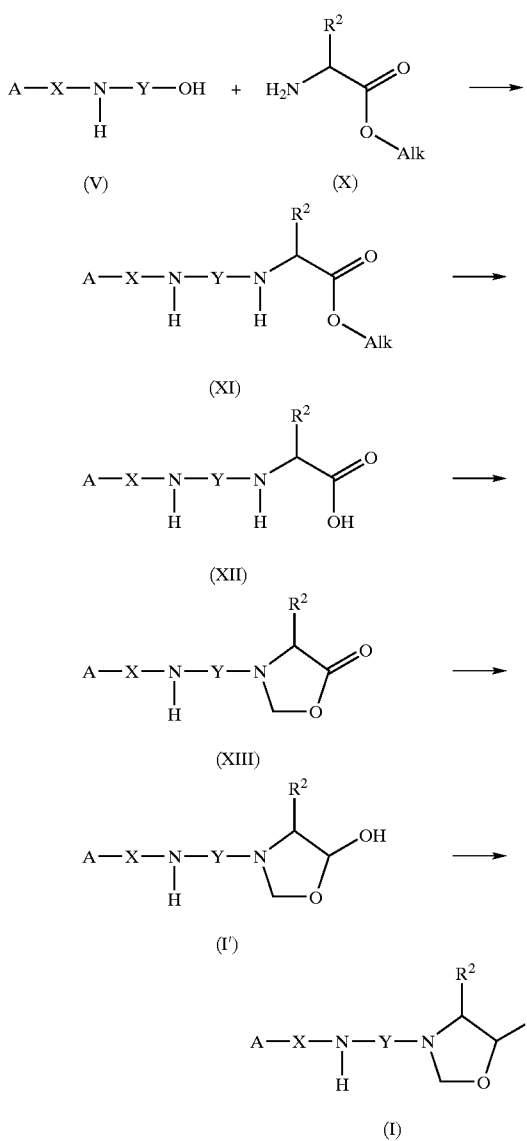

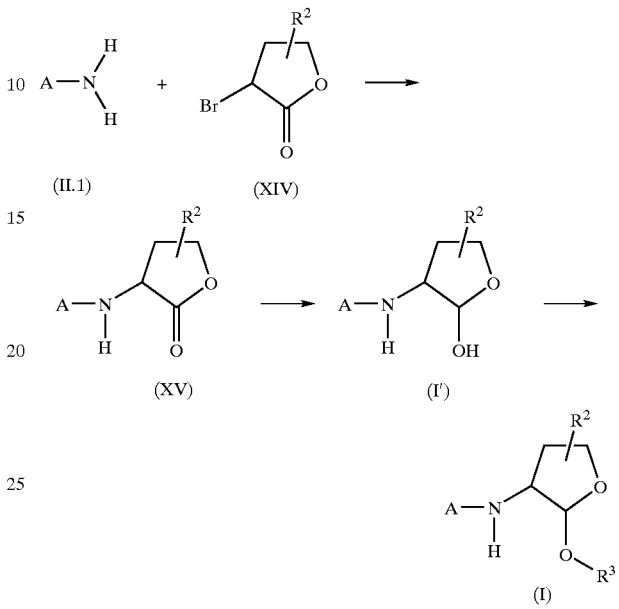

in which A, X, Y, $R^2$ and $R^3$ are as described above, by condensation of the acids of general formula (V) described previously, with the commercial amino-esters of general formula (X) under the peptide synthesis conditions described previously. The esters of general formula (XI) obtained intermediately are then saponified in order to produce carboxylic acids of general formula (XII), which by heating in the presence of paraformaldehyde and of an acid such as, for example, PTSA, while continually trapping the water formed during the reaction using a device of Dean-Stark type, lead to the oxazolidinones of general formula (XIII). These are then reduced using a reducing agent such as, for example, DIBAL, in an inert solvent such as, for example, THF or $CH_2Cl_2$, at a temperature varying from 0 to $-78°$ C. in order to produce oxazolidine derivatives of general formula (I'). The compounds of general formula (I') obtained in this way can be acylated using, for example, an acid chloride ($R^3$—Cl) or an acid anhydride (acetic anhydride, benzoyl chloride, etc.) in the presence of a base such as, for example, triethylamine, in an inert solvent such as for example $CH_2Cl_2$ in order to produce the compounds of formula (I).

The compounds of general formula (I) in which Het represents the tetrahydrofuran ring, X represents the —$(CH_2)_n$— radical (n=0) and Y represents the —$(CH_2)_p$— radical (p=0), can also be prepared according to the following diagram:

in which A, $R^2$ and $R^3$ are as described above, by nucleophilic substitution of the halogen of the lactones of general formula (XV) using the amines of general formula (II.1), while heating the reaction mixture to a temperature varying from 50 to 110° C. in an inert solvent such as for example, acetonitrile or DMF, for a duration varying from 30 minutes to 5 hours, in order to produce the intermediates of general formula (XV). Reduction of the lactone function followed by acylation of the lactol of general formula (I') are carried out under the conditions described previously.

The compounds of general formula (I) in which Het represents the tetrahydrofuran ring, X represents the —$N(R^{45})$—$(CH_2)_n$—CO— radical (n=0) and Y represents the —$(CH_2)_p$— radical (p=0) are ureas which can be prepared according to the following synthesis diagram:

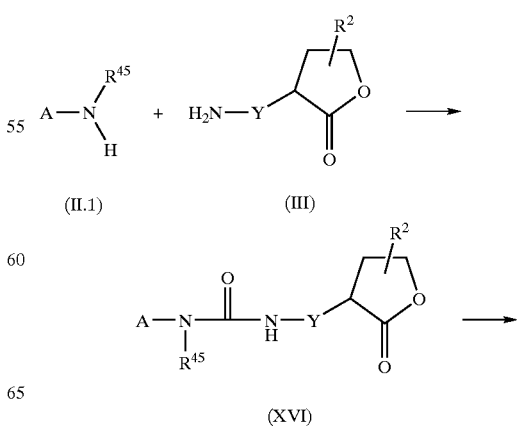

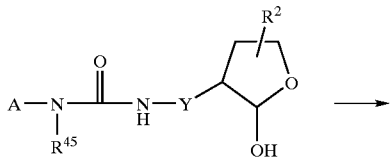

(I')

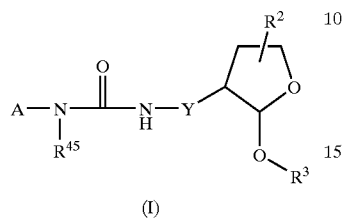

(I)

in which A, $R^2$ and $R^3$ are as described above, by condensation of the amines of general formula (II.1) with the amines of general formula (III) in the presence of triphosgene and of a base such, as, for example, diisopropylethylamine in an inert solvent such as dichloromethane according to an experimental protocol described in J. Org. Chem. (1994) 59 (7), 1937–1938. The lactonic ring of the ureas of general formula (XVI) is then reduced and modified under the experimental conditions described previously in order to produce the compounds of general formula (I).

The compounds of the present invention have useful pharmacological properties: they have an inhibitory activity on calpains and/or a trapping activity on reactive oxygen species.

The compounds of the present invention can thus be used for different therapeutic applications. They can produce beneficial or favourable effects in the treatment of pathologies where these enzymes and/or these radicular species occur.

These properties render the products of formula I suitable for pharmaceutical use. A subject of the present Application is also, as medicaments, the products of formula I as defined above, as well as the addition salts with pharmaceutically acceptable mineral or organic acids or mineral or organic bases of said products of formula I, as well as the pharmaceutical compositions containing, as active ingredient, at least one of the medicaments as defined above.

The invention therefore relates to pharmaceutical compositions containing a compound of the invention or a pharmaceutically acceptable addition salt of the latter, in combination with a pharmaceutically acceptable support. The pharmaceutical composition can be in the form of a solid, for example, powders, granules, tablets, gelatin capsules or suppositories. The appropriate solid supports can be, for example, calcium phosphate, magnesium stearate, talc, sugars, lactose, dextrin, starch, gelatin, cellulose, methyl cellulose, sodium carboxymethyl cellulose, polyvinylpyrrolidine and wax.

The pharmaceutical compositions containing a compound of the invention can also be presented in liquid form, for example, solutions, emulsions, suspensions or syrups. Appropriate liquid supports can be, for example, water, organic solvents such as glycerol or glycols, as well as their mixtures, in varying proportions, in water, added to pharmaceutically acceptable oils or greases. Sterile liquid compositions can be used for intramuscular, intraperitoneal or sub-cutaneous injections and sterile compositions can also be administered intravenously.

Certain compounds of general formula I described previously are covered by the Application EP 641800. The compounds of this Application have an inhibitory activity on cathepsine L which is different from the inhibitory activity on calpains and/or the trapping activity on reactive oxygen species.

A subject of the invention is therefore also the use of compounds of formula $(I_a)$ as defined above,

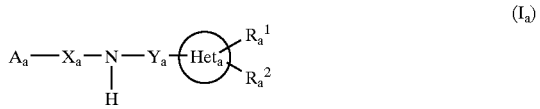

in racemic, enantiomeric, diastereoisomeric form or all combinations of these forms, in which $R_a^1$ represents a hydrogen atom, an —$OR^3$, —$SR^3$, oxo or cyclic acetal radical,
  in which $R^3$ represents a hydrogen atom, an alkyl, arylalkyl, heterocycloalkylcarbonyl, alkylcarbonyl, arylcarbonyl or aralkylcarbonyl radical,
  in which the alkyl, aryl or heterocycloalkyl radicals are optionally substituted by one or more identical or different substituents chosen from: alkyl, OH, alkoxy, nitro, cyano, halogen or —$NR^4R^5$;
$R^4$ and $R^5$ represent, independently, a hydrogen atom or an alkyl radical, or $R^4$ and $R^5$ together with the nitrogen atom to which they are attached form an optionally substituted heterocycle,
$R_a^2$ represents a hydrogen atom, an alkyl, aryl or aralkyl radical, the aryl group being optionally substituted by one or more identical or different radicals chosen from: —$OR^6$, —$NR^7R^8$, halogen, cyano, nitro or alkyl,
  in which $R^6$, $R^7$ and $R^8$ represent, independently, a hydrogen atom, an alkyl, aryl, aralkyl, alkylcarbonyl, arylcarbonyl or aralkylcarbonyl radical;
$A_a$ represents
  either an A1 or A'1 radical

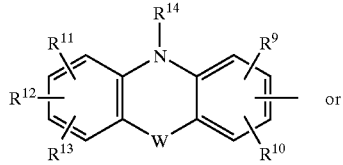

A1 or

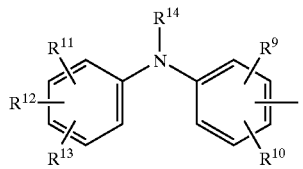

A'1 in which $R^9$, $R^{10}$, $R^{11}$, $R^{12}$, $R^{13}$ represent, independently, a hydrogen atom, a halogen, the OH group, an alkyl, alkoxy, cyano, nitro or —$NR^{15}R^{16}$ radical,
$R^{15}$ and $R^{16}$ represent, independently, a hydrogen atom, an alkyl radical or a —$COR^{17}$ group, or $R^{15}$ and $R^{16}$ together with the nitrogen atom to which they are attached form an optionally substituted heterocycle,
$R^{17}$ represents a hydrogen atom, an alkyl, alkoxy or —$NR^{18}R^{19}$ radical,
$R^{18}$ and $R^{19}$ represent, independently, a hydrogen atom or an alkyl radical, or $R^{18}$ and $R^{19}$ together with the nitrogen atom to which they are attached form an optionally substituted heterocycle,
$R^{14}$ represents a hydrogen atom, an alkyl radical or a —$COR^{20}$ group,
$R^{20}$ represents a hydrogen atom, an alkyl, alkoxy, aryl, aralkyl, heterocycloalkyl or —$NR^{21}R^{22}$ radical,
  in which the alkyl, aryl or heterocycloalkyl radicals are optionally substituted by one or more identical or different substituents chosen from: alkyl, OH, alkoxy, nitro, cyano, halogen or —$NR^4R^5$;

$R^{21}$ and $R^{22}$ represent, independently, a hydrogen atom or an alkyl radical, or $R^{21}$ and $R^{22}$ together with the nitrogen atom to which they are attached form an optionally substituted heterocycle, W represents a bond, O or S or also an —$NR^{23}$ radical, in which $R^{23}$ represents a hydrogen atom or an alkyl radical;

or an A2 radical

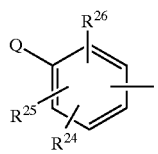

in which
$R^{24}$, $R^{25}$ and $R^{26}$ represent, independently, a hydrogen, a halogen, the OH or $SR^{27}$ group, an alkyl, alkenyl, alkoxy radical or an —$NR^{28}R^{29}$ radical,
$R^{27}$ represents a hydrogen atom or an alkyl radical,
$R^{28}$ and $R^{29}$ represent, independently, a hydrogen atom, an alkyl radical or a —$COR^{30}$ group, or $R^{28}$ and $R^{29}$ together with the nitrogen atom to which they are attached form an optionally substituted heterocycle,
$R^{30}$ represents a hydrogen atom, an alkyl, alkoxy or —$NR^{31}R^{32}$ radical,
$R^{31}$ and $R^{32}$ represent, independently, a hydrogen atom or an alkyl radical, or $R^{31}$ and $R^{32}$ together with the nitrogen atom to which they are attached form an optionally substituted heterocycle,
Q represents —$OR^{33}$, —$SR^{33}$, —$NR^{34}R^{35}$ or an aryl radical substituted by one or more identical or different substituents chosen from: halogen, the OH group, an alkyl, alkoxy, cyano, nitro or —$NR^{15}R^{16}$ radical,
$R^{33}$ represents a hydrogen atom, an alkyl, arylalkyl, heterocycloalkylcarbonyl, alkylcarbonyl, arylcarbonyl or aralkylcarbonyl radical,
in which the alkyl, aryl or heterocycloalkyl radicals are optionally substituted by one or more identical or different substituents chosen from: alkyl, OH, alkoxy, nitro, cyano, halogen or —$NR^4R^5$;
$R^{34}$ and $R^{35}$ represent, independently, a hydrogen atom, an alkyl radical or a —CO—$R^{36}$ radical, or together with the nitrogen atom to which they are attached form an optionally substituted heterocycle,
$R^{36}$ representing an alkyl radical;

or an A3 radical

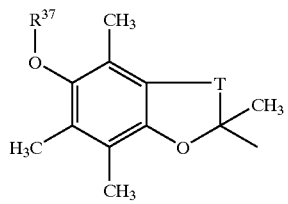

in which $R^{37}$ represents a hydrogen atom, an alkyl, arylalkyl, heterocycloalkylcarbonyl, alkylcarbonyl, arylcarbonyl or aralkylcarbonyl radical,
in which the alkyl, aryl or heterocycloalkyl radicals are optionally substituted by one or more identical or different substituents chosen from: alkyl, OH, alkoxy, nitro, cyano, halogen or —$NR^4R^5$;
T represents a —$(CH_2)_m$— radical with m=1 or 2;

or an A4 radical

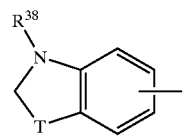

in which $R^{38}$ represents a hydrogen atom, an alkyl, —$(CH_2)_q$—$NR^{39}R^{40}$ or aralkyl radical, the aryl group being optionally substituted by one or more identical or different substituents chosen from: OH, alkyl, halogen, nitro, alkoxy or —$NR^{39}R^{40}$,
q being an integer comprised between 2 and 6;

or an A5 radical

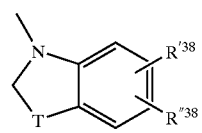

in which $R'^{38}$ and $R''^{38}$ represent independently a hydrogen atom, nitro, —$NR'^{39}R'^{40}$, an alkyl or arylalkyl radical, the aryl group being optionally substituted by one or more identical or different substituents chosen from: OH, the alkyl, halogen, nitro, alkoxy or —$NR^{39}R^{40}$ radicals,
$R'^{39}$, $R'^{40}$, $R^{39}$ and $R^{40}$ represent, independently, a hydrogen atom, an alkyl radical or a —$COR^{41}$ group, or $R^{39}$ and $R^{40}$ or $R'^{39}$ and $R'^{40}$ together with the nitrogen atom form an optionally substituted heterocycle,
$R^{41}$ represents a hydrogen atom, an alkyl, alkoxy or —$NR^{42}R^{43}$ radical,
$R^{42}$ and $R^{43}$ represent, independently, a hydrogen atom or an alkyl radical, or $R^{42}$ and $R^{43}$ together with the nitrogen atom to which they are attached form an optionally substituted heterocycle,
T representing a —$(CH_2)_m$— radical with m=1 or 2, or finally an A6 radical

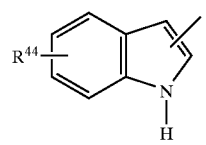

in which $R^{44}$ represents a hydrogen atom, the OH group or an alkyl or alkoxy radical;
$X_a$ represents —$(CH_2)_n$—, —$(CH_2)_n$—CO—, —N($R^{45}$)—CO—$(CH_2)_n$—CO—,—N($R^{45}$)—CO—D—CO—, —CO—N($R^{45}$)—D—CO—, —CO—D—CO—, —CH=CH—$(CH_2)_n$—CO—, —N($R^{45}$)—$(CH_2)_n$—CO—, —N($R^{45}$)—CO—C($R^{46}R47$)—CO—, —O—$(CH_2)_n$—CO—, —N($R^{45}$)—CO—NH—C($R^{46}R^{47}$)—CO—, —CO—N($R^{45}$)—C($R^{46}R^{47}$)—CO—, —S—$(CH_2)_n$—CO— or —Z—CO—;
D represents a phenylene radical optionally substituted by one or more identical or different radicals chosen from alkyl, alkoxy, OH, nitro, halogen, cyano, or carboxyl to optionally esterified by an alkyl radical;
Z represents a heterocycle,
$R^{45}$ represents a hydrogen atom or an alkyl radical,
$R^{46}$ and $R^{47}$ represent, independently, a hydrogen atom, an alkyl, aryl or aralkyl radical the alkyl and aryl groups of which are optionally substituted by one or more identical or different substituents chosen from: the OH, —SH, halogen, nitro, alkyl, alkoxy, alkylthio, aralkoxy, aryl-alkylthio, —NR$^{48}$R$^{49}$ and carboxyl group optionally esterified by an alkyl radical;

R$^{48}$ and R$^{49}$ represent, independently, a hydrogen atom, an alkyl radical or a —COR$^{50}$ group, or R$^{48}$ and R$^{49}$ together with the nitrogen atom to which they are attached form an optionally substituted heterocycle, R$^{50}$ represents a hydrogen atom, an alkyl, alkoxy or —NR$^{51}$R$^{52}$ radical, R$^{51}$ and R$^{52}$ represent, independently, a hydrogen atom or an alkyl radical, or R$^{51}$ and R$^{52}$ together with the nitrogen atom to which they are attached form an optionally substituted heterocycle;

n being an integer comprised between 0 and 6;

Y$_a$ represents —(CH$_2$)$_p$—, —C(R$^{53}$R$^{54}$)—(CH$_2$)$_p$—, —C(R$^{53}$R$^{54}$)—CO—;

R$^{53}$ and R$^{54}$ represent, independently, a hydrogen atom, an alkyl radical, an aralkyl radical the aryl group of which is optionally substituted by one or,more identical or different substituents chosen from: the OH group, halogen, nitro, alkyl, alkoxy, —NR$^{55}$R$^{56}$, R$^{55}$ and R$^{56}$ represent, independently, a hydrogen atom, an alkyl radical or a —COR$^{57}$ group, or R$^{55}$ and R$^{56}$ together with the nitrogen atom to which they are attached form an optionally substituted heterocycle, R$^{57}$ represents a hydrogen atom, an alkyl, alkoxy or —NR$^{58}$R$^{59}$ radical, R$^{58}$ and R$^{59}$ represent, independently, a hydrogen atom or an alkyl radical, or R$^{58}$ and R$^{59}$ together with the nitrogen atom to which they are attached form an optionally substituted heterocycle;

p being an integer comprised between 0 and 6;

Het$_a$ represents a heterocycle, as well as addition salts with mineral and organic acids or with mineral and organic bases of said compounds of general formula (I), for the preparation of medicaments for the treatment of pathologies where calpains and/or reactive oxygen species are involved.

A more particular subject of the invention is the use of compounds of formula (I$_a$) as defined above, for the preparation of medicaments for the treatment of pathologies involving reactive oxygen species. A more particular subject of the invention is also the use of compounds of formula (I$_a$) as defined above, for the preparation of medicaments for the treatment of pathologies involving reactive oxygen species and calpains. The invention therefore relates to the use of compounds of formula (I$_a$) as defined above, for the preparation of medicaments for the treatment of pathologies such as inflammatory and immunological diseases, cardiovascular and cerebrovascular diseases, disorders of the central or peripheral nervous system, osteoporosis, muscular dystrophy, proliferative diseases, cataracts, organ transplants, auto-immune and viral diseases, cancer, and all pathologies characterized by an excessive production of ROS's and/or the activation of calpains.

A more particular subject of the invention is the use of compounds of formula (I$_a$) as defined above, characterized in that Het represents a monocyclic radical containing 1 to 2 heteroatoms chosen from O and N. Preferentially, Het represents tetrahydrofuran, dioxolane, pyrrolidine, 1,3-oxazolidine, and R$^1$ represents the hydrogen atom, the —OR$^3$ or oxo radical.

A more particular subject of the invention is the use of compounds of formula (I$_a$) as defined above, characterized in that X represents —(CH$_2$)$_n$—, —(CH$_2$)$_n$—CO—, —O—(CH$_2$)$_n$—CO—, —CO—N(R$^{45}$)—D—CO—, —Z—CO—, —N(R$^{45}$)—CO—(CH$_2$)$_n$—CO—, —N(R$^{45}$)—CO—C(R$^{46}$R$^{47}$)—CO—, —N(R$^{45}$)—(CH$_2$)$_n$—CO—, —N(R$^{45}$)—CO—NH—C(R$^{46}$R$^{47}$)—CO— or —CO—N(R$^{45}$)—C(R$^{46}$R$^{47}$)—CO and preferentially when R$^{45}$ and R$^{47}$ represent the hydrogen atom, R$^{46}$ represents the hydrogen atom, an alkyl or phenyl radical, D represents the phenylene radical and Z represents the thiazole radical.

A more particular subject of the invention is the use of compounds of formula (I$_a$) as defined above characterized in that R$^2$ represents a hydrogen atom or an aralkyl radical, and preferably the benzyl radical.

A more particular subject of the invention is the use of compounds of formula (I$_a$) as defined above characterized in that A represents either A1 with W representing the sulphur atom; or A'1; or A2 together with R$^{24}$, R$^{25}$ and R$^{26}$ which represent, independently, a hydrogen or an alkyl radical and Q which represents —OR$^{33}$; or A3 together with T representing the —(CH$_2$)$_2$— radical; or A4 together with T representing the —(CH$_2$)— radical. Preferably, A represents a radical chosen from

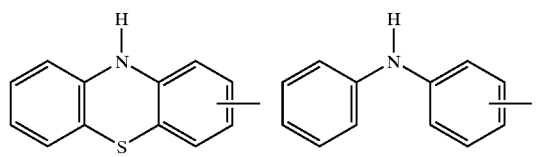

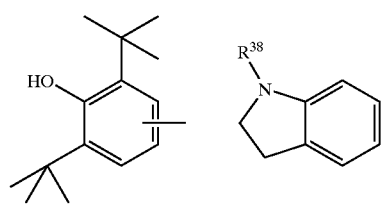

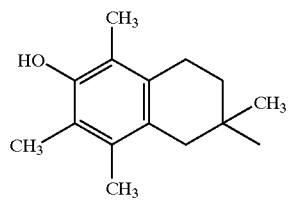

A more particular subject of the invention is also the use as defined above, of compounds of formula (I$_a$) as described in the examples and preferentially the compounds which correspond to one of the following formulae:

(2R)-6-hydroxy-N-[(3S)-2-hydroxytetrahydro-3-furanyl]-2,5,7,8-tetramethyl-3,4-dihydro-2H-chromene-2-carboxamide;

N-1-(4-anilinophenyl)-N-4-[(3S)-2-hydroxytetrahydro-3-furanyl]succinamide;

(3S)-3-{[4-(4-anilinoanilino)-4-oxobutanoyl]amino}tetrahydro-2-furanyl acetate;

N-1-(4-anilinophenyl)-N-4-[(1S)-1-(1,3-dioxolan-2-yl)-3-methylbutyl]succinamide;

N-1-(4-anilinophenyl)-N-3-[(3S)-2-hydroxytetrahydro-3-furanyl]-2-phenylmalonamide;

3-(4-anilinoanilino)tetrahydro-2-furanol;

N-[(1S)-1-({[(3S)-2-hydroxytetrahydro-3-furanyl]amino}carbonyl)-3-methylbutyl]-10H-phenothiazine-2-carboxamide;

(3S)-3-({(2S)-4-methyl-2-[(10H-phenothiazin-2-ylcarbonyl)amino]pentanoyl}amino)tetrahydro-2-furanyl acetate;

N-[(3S)-2-hydroxytetrahydro-3-furanyl]-2-(10H-phenothiazin-2-yl)-1,3-thiazol-4-carboxamide;

N-[4-({[(3S)-2-hydroxytetrahydro-3-furanyl]amino}carbonyl)phenyl]-10H-phenothiazine-2-carboxamide;

N-[(1S)-1-({[(3S)-2-hydroxytetrahydro-3-furanyl]amino}carbonyl)-3-methylbutyl]-10H-phenothiazine-1-carboxamide;

(3S)-3-({(2S)-4-methyl-2-[(10H-phenothiazin-2-ylcarbonyl)amino]pentanoyl}amino)tetrahydro-2-furanyl pivalate;

(3S)-3-({(2S)-4-methyl-2-[(10H-phenothiazin-2-ylcarbonyl)amino]pentanoyl}amino)tetrahydro-2-furanyl 3,3-dimethylbutanoate;

(3S)-3-({(2S)-4-methyl-2-[(10H-phenothiazin-2-ylcarbonyl)amino]pentanoyl}amino)tetrahydro-2-furanyl benzoate;

(3S)-3-({(2S)-4-methyl-2-[(10H-phenothiazin-2-ylcarbonyl)amino]pentanoyl}amino)tetrahydro-2-furanyl phenylacetate;

(3S)-3-({(2S)-4-methyl-2-[(10H-phenothiazin-2-ylcarbonyl)amino]pentanoyl}amino)tetrahydro-2-furanyl (2S)-2-(dimethylamino)-3-phenylpropanoate;

(3S)-3-({(2S)-4-methyl-2-[(10H-phenothiazin-2-ylcarbonyl)amino]pentanoyl}amino)tetrahydro-2-furanyl 4-morpholinecarboxylate;

N-{(1S)-3-methyl-1-[(3-oxo-1-pyrrolidinyl)carbonyl]butyl}-10H-phenothiazine-2-carboxamide;

2-(3,5-di-tert-butyl-4-hydroxyphenoxy)-N-[(3S)-2-hydroxytetrahydro-3-furanyl]acetamide;

$N^1$-[(3S)-2-hydroxytetrahydro-3-furanyl]-2-phenyl-$N^3$-(1-propyl-2,3-dihydro-1H-indol-5-yl)malonamide;

N-(2-anilinophenyl)-N'-[(3S)-2-hydroxytetrahydro-3-furanyl]urea;

$N^1$-[(3S)-2-hydroxytetrahydro-3-furanyl]-$N^2$-(1-propyl-2,3-dihydro-1H-indol-5-yl)ethanediamide;

(2R)-N-[(1S)-1-(1,3-dioxolan-2-yl)-2-phenylethyl]-6-hydroxy-2,5,7,8-tetramethyl-3,4-dihydro-2H-chromene-2-carboxamide;

N-[(3S)-2-hydroxytetrahydro-3-furanyl]-5-indolinecarboxamide.

The non-commercial synthesis intermediates of formula (II), (III) and (V) can be prepared according to the different synthesis routes below:

1) Synthesis of Intermediates (II)

The carboxylic acids of general formula (II), in which A, X, D, n, $R^{45}$, $R^{46}$ and $R^{47}$ are as described above, are accessible from the following synthetic diagrams:

1.1) Starting from A-NH($R^{45}$)

The preparation of carboxylic acids of general formula (II) can be carried out, in this case, from 3 different acid-ester derivatives (II.2), (II.4) and (II.6):

The condensation of the anilines of general formula (II.1) with commercial acid-esters (Alk=Alkyl) of general formula (II.2), Diagram 1.1, is carried out by standard peptide condensation. The carboxamide obtained intermediately (II.3) is then saponified in order to produce the carboxylic acids of general formula (II). The synthesis of the intermediates of general formula (II.1) is described below.

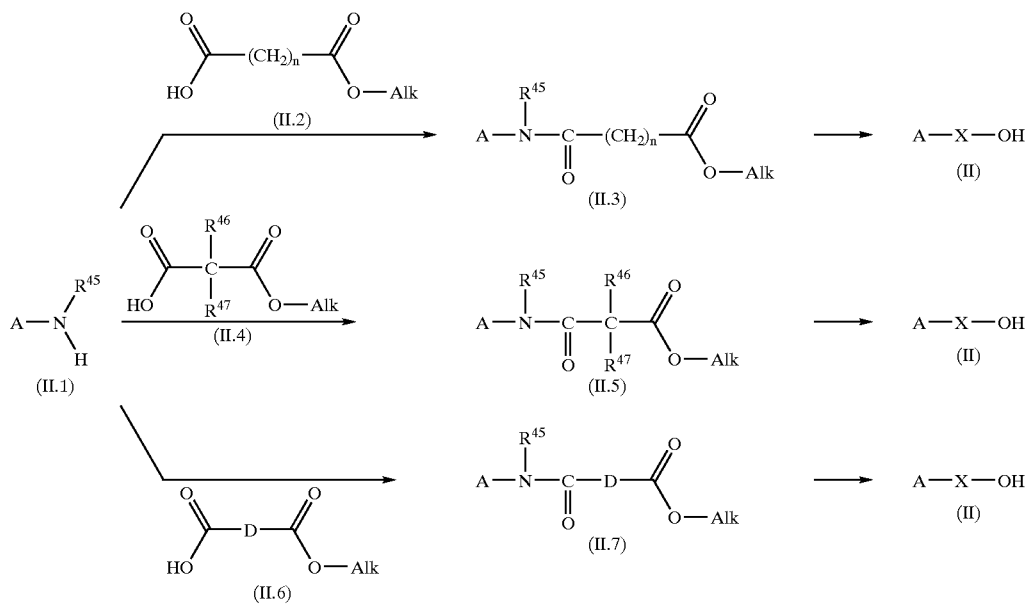

Diagram 1.1

The synthesis of the carboxylic acids of general formula (II) can also be carried out by condensation of the anilines of general formula (II.1) with the acid-ester derivatives of general formula (II.4) under the conditions described previously. This condensation is followed by standard saponification in order to produce acids of general formula (II). The synthesis of intermediates of general formula (II.4) is described below.

The condensation of the amines of general formula (II.1) with the commercial aromatic acids of general formula (II.6), under standard peptide synthesis conditions described already, after saponification of the intermediates of general formula (II.7) also leads to carboxylic acids of general formula (II).

Alternatively, the carboxylic acids of general formula (II) are also accessible by opening cyclic anhydrides such as for example succinic anhydride, using the amines of general formula (II.1) according to an experimental protocol described in the literature (J. Amer. Chem. Soc. (1951) 73, 4007).

1.1.1) Preparation of Intermediates (II.1)

The non-commercial anilines of general formula (II.1), derivatives of indoline or 1,2,3,4-tetrahydroquinoline, Diagram 1.1.1, in which T and $R^{38}$ are as defined above, can be prepared from the corresponding nitro derivatives of general formula (II.1.1). 6-nitro-1,2,3,4-tetrahydroquinoline is described in Can. J. Chem. (1952), 30, 720–722. Alkylation of the amine is carried out in a standard fashion using a strong base such as, for example, NaH, in a polar aprotic solvent such as, for example, DMF in the presence of a halogenated derivative $R^{38}$-Hal, such as for example 3-dimethylaminopropanol chloride or benzyl bromide. The nitro derivative of general formula (II.1.2) obtained intermediately is then reduced, for example, by Raney Nickel in the presence of hydrazine hydrate in order to produce the anilines of general formula (II.1).

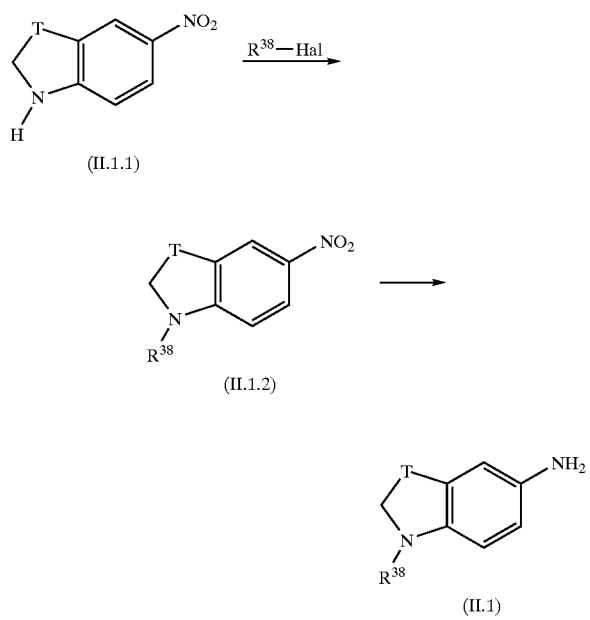

Moreover, certain non-commercial derivatives of phenylenediamines of general formula (II.1) can be prepared according to Farmaco (1951) 6,713–717.

In the particular case where A is a phenolic derivative (A=A2), the anilines of general formula (II.1) are obtained by hydrogenation, in the presence of Pd/C, of the nitrophenol derivative precursors. The nitrated derivatives of di-alkyl phenols are accessible according to the methods described in J. Org. Chem. (1968) 33 (1), 223–226 or J. Med. Chem. (1998), 41, 1846–1854.

The intermediates of general formula (II.1) in which A'1 is a diphenylamine are accessible via the methods described in the literature (Synthesis (1990) 430; Indian J. Chem. (1981) 20B, 611–613; J. Med. Chem. (1975) 18 (4), 386–391) which involve the reduction of a nitrodiphenylamine intermediate. Reduction of the nitro function is carried out in a standard fashion by hydrogenation in the presence of a catalytic quantity of Pd/C in order to access the aminodiphenylamines of general formula (II.1).

When A is a carbazole derivative (W then represents a direct bond), the methods for preparing the aminocarbazoles of general formula (II.1) involve the synthesis of a nitrocarbazole intermediate. These methods are described in Pharmazie (1993) 48 (11), 817–820; Synth. Commun. (1994) 24(1), 1–10; J. Org. Chem. (1980),45, 1493–1496; J. Org. Chem. (1964) 29 (8), 2474–2476; Org. Prep. Proced. Int. (1981) 13 (6), 419–421 or J. Org. Chem. (1963) 28, 884. Reduction of the nitro function of the nitrocarbazole intermediates is, in this case, preferably carried out using hydrazine hydrate in the presence of Raney Nickel.

The intermediates of general formula (II.1) in which A is a phenothiazine derivative (W represents a sulphur atom), are accessible via methods in the literatures which involve the synthesis of a nitrophenothiazine derivative. In particular 3-nitrophenothiazine is described in J. Org. Chem. (1972) 37, 2691. The reduction of the nitro function in order to access the aminophenothiazines of general formula (II.1) is carried out in a standard fashion by hydrogenation in the presence of a catalytic quantity of Pd/C in a solvent such as ethanol.

1.1.2) Preparation of Intermediates (II.4)

The acid-esters of general formula (II.4), Diagram 1.1.2, can be prepared from the commercial diesters of general formula (II.4.1) according to a method described in the literature (Tetrahedron Asymmetry (1997) 8(11), 1821–1823).

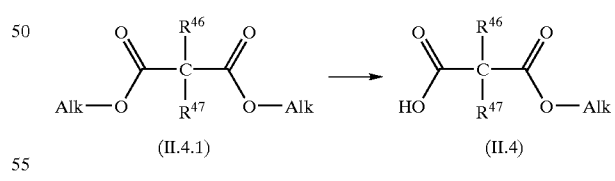

1.2) Starting from A-CO$_2$H

The carboxylic acid intermediates of general formula (II) are also accessible via the condensation of the carboxylic acids of general formula (II.8) with the commercial aminoesters of general formula (II.9A) or (II.9B), Diagram 1.2, during a peptide synthesis stage described previously. The carboxamides obtained intermediately (II.10A) and (II.10B) are then saponified in order to produce the carboxylic acids of general formula (II).

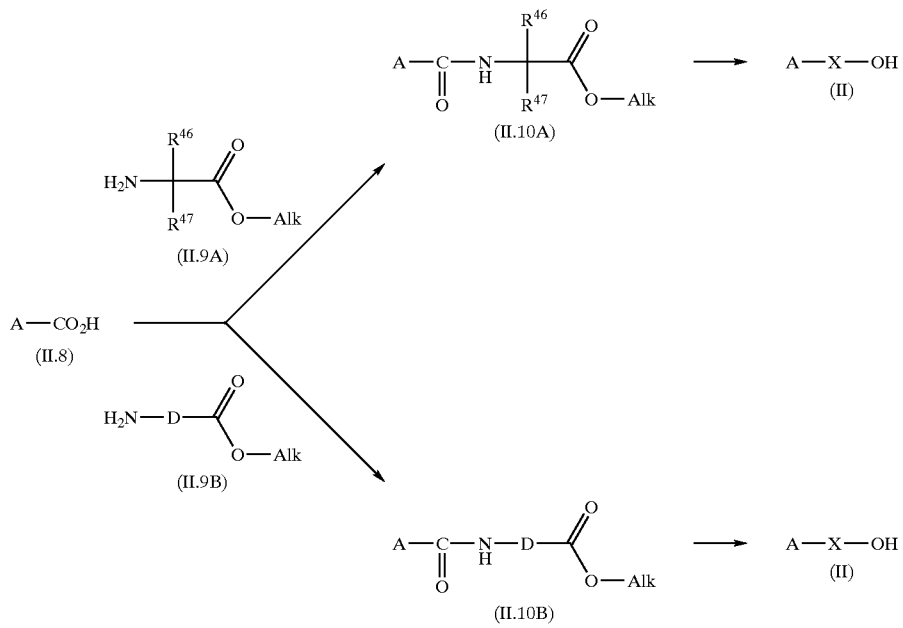

1.2.1) Preparation of Intermediates (II.8)

The carboxylic derivatives of general formula (II.8), which are not commercially accessible, can be prepared from the literature (e.g.: J. Org. Chem. (1961) 26, 1221–1223; Acta Chem. Scandinavica (1973) 27, 888–890; Can. J. Chem. (1972),50, 1276–1282; J. Med. Chem. (1992) 35(4), 716–724; J. Org. Chem. (1989) 54, 560–569; J. Med. Chem. (1998) 41(2), 148–156; Bull. Soc. Chim. Fr. (1960), 1049–1066)).

1.3) Starting from A-OH or A-SH

The acids of general formula (II) (Diagram 1.3) in which X represents $-O-(CH_2)_n-CO-$, are prepared from the hydroquinones of general formula (II.11) obtained according to the literature (J. Chem. Soc. Perkin 1 (1981) 303–306). The condensation on commercial halogen esters of general formula (II.12) is carried out in the presence of a base such as, for example $K_2CO_3$, by heating in a polar solvent such as, for example, THF for at least 5 hours. The esters of general formula (II.13) intermediately obtained are then deprotected (in an acid medium in the case of tert-butyl esters) in order to produce acids of general formula (II).

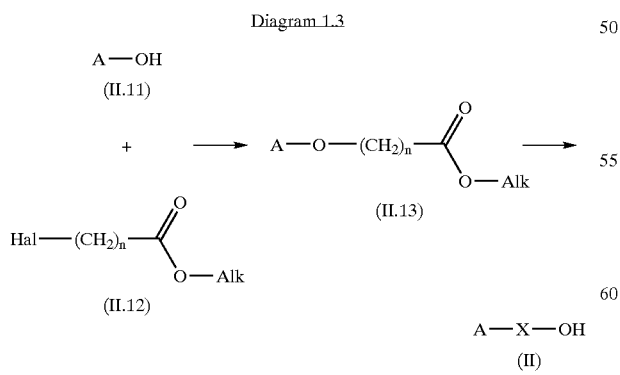

Diagram 1.3

The acids of general formula (II) in which X represents $-S-(CH_2)_n-CO-$, are prepared according to a method in the literature (J. Med. Chem. (1997) 40(12), 1906–1918).

1.4) Starting from $A-CO_2H$, when Z represents a heterocycle with V=S or O 1.4.a) In the case where Z represents an unsaturated heterocycle, the carboxylic acids of general formula (II), Diagram 1.4a, can be prepared from carboxylic acids of general formula (II.8).

Diagram 1.4a

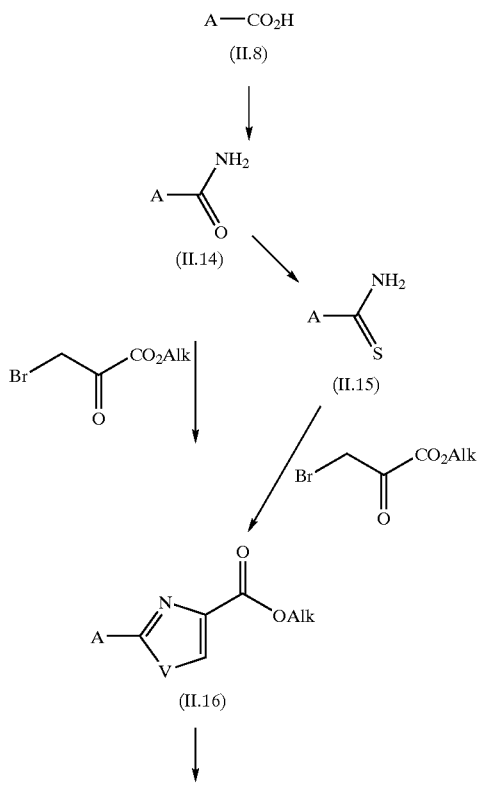

-continued

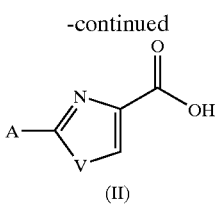

(II)

The formation of the primary carboxamide of general formula (II.14) is carried out according to an experimental protocol described in the literature (Synthesis (1989), 1, 37). By heating, between 50° C. and reflux of the solvent, for a time comprised between 1 and 15 hours, intermediate (II.14) in the presence of an alkyl bromopyruvate, the oxazoles (V=O) of general formula (II.16) are obtained. Alternatively, the thiazoles (V=S) of general formula (II.16), are accessible in two stages from the carboxamides of general formula (II.14). These, in the presence of Lawesson's reagent in a solvent such as, for example, 1,4-dioxane, lead in a standard fashion to the thiocarboxamides of general formula (II.15). The cyclization stage is then carried out in the presence of alkyl bromopyruvate as described previously. The carboxylic acids of general formula (II) are finally obtained by deprotection of the acid function under standard conditions.

1.4.b) In the case where Z represents a saturated heterocycle, and in particular a thiazolidine, the carboxylic acids of general formula (II), Diagram 1.4b, are also accessible from the carboxylic acids of general formula (II.8).

Diagram 1.4b

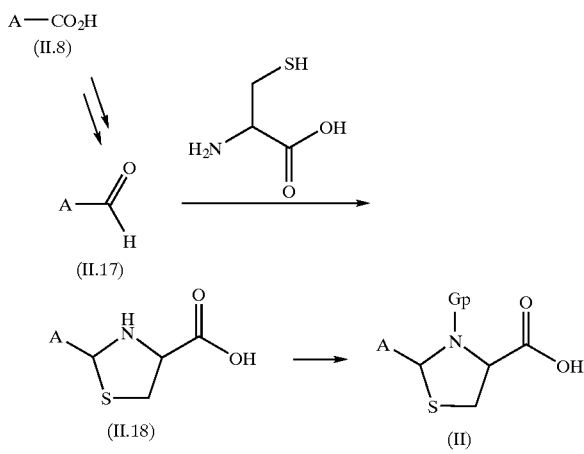

The preparation of the aldehydes of general formula (II.17) is carried out in a standard fashion after activation of the acid function of the intermediates of general formula (II.8) in the form of an ester or an alkylhydroxamate, in the presence of DIBAL or of LiAlH$_4$, according to the experimental protocols in the literature (e.g. J. Med. :Chem. (1990) 33, 11–13). The reaction of these aldehydes with cysteine in the presence of acetate salts leads directly to the thiazolidines of general formula (II.18) according to an experimental protocol described in J. Org. Chem. (1957) 22, 943–946. The amine of the thiazolidine ring is then protected in the form of a carbamate (e.g. Boc) under standard conditions in the literature in order to produce the carboxylic acids of general formula (II).

1.5) Starting from A-N(R$^{45}$)—CO—

The carboxylic acids of general formula (II), in which X=—N(R$^{45}$)—(CH$_2$)$_n$—CO— with n=0, are constituted by a chain functionalized by a urea, Diagram 1.5.

Diagram 1.5

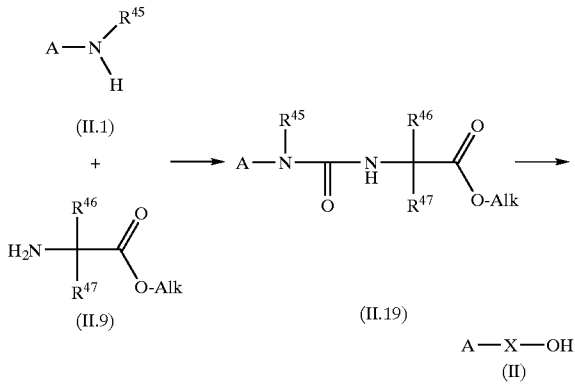

The synthesis of these ureas is carried out by condensation of the amines of general formula (II.1) with the aminoesters of general formula (II.9) in the presence of triphosgene and a tertiary amine according to an experimental protocol described in the literature (J. Org. Chem. (1994), 59(7), 1937–1938) in order to produce the intermediates of general formula (II.19). The carboxylic acid of general formula (II) is then obtained in a standard fashion by deprotection of the intermediate ester.

2) Synthesis of Intermediates (III)

The preparation of intermediates of general formula (III), Diagram 1.4, in which R$^2$ is as defined above and Y=—(CH$_2$)$_p$—, with p=0, is carried out from derivatives of N-Cbz aspartic acid of general formula (III.1) access to which is described in the literature (J. Med. Chem. (1973) 16(11), 1277–1280). By heating these intermediates in the presence of trioxane and a catalytic quantity of PTSA under reflux of a solvent such as, for example, toluene, (Synthesis (1989) 7, 542–544) the oxazolidinone derivatives of general formula (III.2) are obtained. Reduction of the acid function is then carried out using B$_2$H$_6$.THF in THF as described in Chem. Pharm. Bull. (1995) 43 (10), 1683–1691 and leads to alcohols of general formula (III.3). These are then treated in a basic medium, and intermediate (III.4) generated in this way is cyclized using a standard dehydration agent such as, for example, dicyclohexylcarbodiimide in order to obtain the substituted lactone of general formula (III.5). The intermediate of general formula (III) is obtained after cleavage of the benzyl carbamate using Pd/C under a hydrogen atmosphere.

Diagram 2

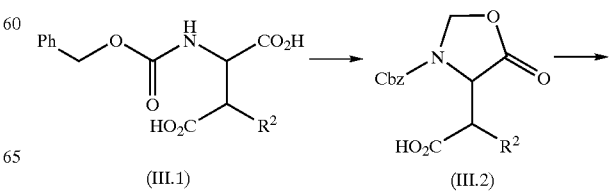

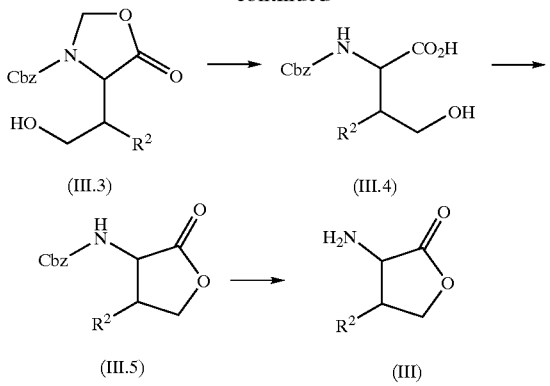

3) Synthesis of Intermediates (V)

The intermediates of general formula (V) (Diagram 2.1), in which A, X, Y, $R^{53}$ and $R^{54}$ are as described above, are prepared in a standard fashion by peptide condensation of the acids of general formula (II), described previously, with commercial amino-esters of general formula (V.1). Carboxylic acids of general formula (V) are obtained after saponification of the intermediate esters of general formula (V.2).

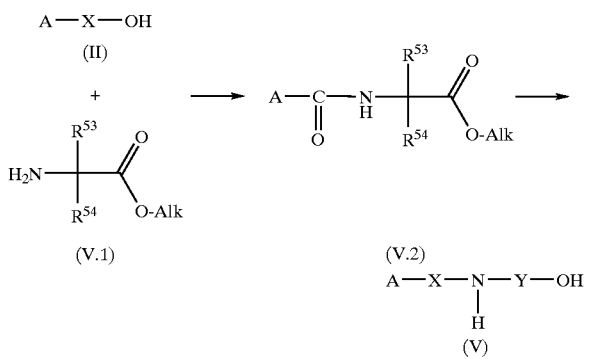

A subject of the invention is also, as new industrial products, and in particular as new industrial products intended for the preparation of products of formula I, the products corresponding to one of the following formulae:

N-1-(4-anilinophenyl)-N-4-[(3S)-2-oxotetrahydro-3-furanyl]succinamide;
methyl (2S)-2-{([4-(4-anilinoanilino)-4-oxobutanoyl]amino}-4-methylpentanoate;
N1-(4-anilinophenyl)-N4-[(1S)-1-formyl-3-methylbutyl]succinamide;
benzyl 3-(4-anilinoanilino)-3-oxo-2-phenylpropanoate;
3-(4-anilinoanilino)-3-oxo-2-phenylpropanoic acid;
N-1-(4-anilinophenyl)-N-3-[(3S)-2-oxotetrahydro-3-furanyl]-2-phenylmalonamide;
3-(4-anilinoanilino)dihydro-2(3H)-furanone;
methyl (2S)-4-methyl-2-[(10H-phenothiazin-2-ylcarbonyl)amino]pentanoate;
(2S)-4-methyl-2-[(10H-phenothiazin-2-ylcarbonyl)amino]pentanoic acid;
N-[(1S)-3-methyl-1-({[(3S)-2-oxotetrahydro-3-furanyl]amino}carbonyl)butyl]-10H-phenothiazine-2-carboxamide;
ethyl 2-(10H-phenothiazin-2-yl)-1,3-thiazol-4-carboxylate;
2-(10H-phenothiazin-2-yl)-1,3-thiazol-4-carboxylic acid;
N-[(3S)-2-oxotetrahydro-3-furanyl]-2-(10H-phenothiazin-2-yl)-1,3-thiazol-4-carboxamide;
methyl 4-[(10H-phenothiazin-2-ylcarbonyl)amino]benzoate;
4-[(10H-phenothiazin-2-ylcarbonyl)amino]benzoic acid;
N-[4-({[(3S)-2-oxotetrahydro-3-furanyl]amino}carbonyl)phenyl]-10H-phenothiazine-2-carboxamide;
methyl (2S)-4-methyl-2-[(10H-phenothiazin-1-ylcarbonyl)amino]pentanoate;
(2S)-4-methyl-2-[(10H-phenothiazin-1-ylcarbonyl)amino]pentanoic acid;
N-[(1S)-1-({[(3S)-2-oxotetrahydro-3-furanyl]amino}carbonyl)-3-methylbutyl]-10H-phenothiazine-1-carboxamide;
N-[(1S)-1-(1,4-dioxa-7-azaspiro[4.4]non-7-ylcarbonyl)-3-methylbutyl]-10H-phenothiazine-2-carboxamide;
2-(3,5-di-tert-butyl-4-hydroxyphenoxy)-N-[(3S)-2-oxotetrahydro-3-furanyl]acetamide
5-nitro-1-propylindoline;
1-propyl-2,3-dihydro-1H-indol-5-ylamine;
3-oxo-2-phenyl-N-(1-propyl-2,3-dihydro-1H-indol-5-yl)-beta-alanine;
$N^1$-[(3S)-2-oxotetrahydro-3-furanyl]-2-phenyl-$N^3$-(1-propyl-2,3-dihydro-1H-indol-5-yl)malonamide;
N-(2-anilinophenyl)-N'-[(3S)-2-oxotetrahydro-3-furanyl]urea;
ethyl oxo[(1-propyl-2,3-dihydro-1H-indol-5-yl)amino]acetate;
oxo[(1-propyl-2,3-dihydro-1H-indol-5-yl)amino]acetic acid;
methyl (2S)-2-({[(2R)-6-hydroxy-2,5,7,8-tetramethyl-3,4-dihydro-2H-chromen-2-yl]carbonyl}amino)-3-phenylpropanoate;
(2R)-N-[(1S)-1-benzyl-2-oxoethyl]-hydroxy-2,5,7,8-tetramethyl-3,4-dihydro-2H-chromene-2-carboxamide;
tert-butyl 5-methyl 1,5-indolinedicarboxylate;
1-(tert-butoxycarbonyl)-5-indolinecarboxylic acid;
tert-butyl 5-({[(3S)-2-oxotetrahydro-3-furanyl]amino}carbonyl)-1-indolinecarboxylate;
tert-butyl 5-({[(3S)-2-hydroxytetrahydro-3-furanyl]amino}carbonyl)-1-indolinecarboxylate.

Experimental Part

The following examples are presented in order to illustrate the above procedures and should in no event be considered as a limit to the scope of the invention.

EXAMPLE 1

(2R)-6-hydroxy-N-[(3S)-2-hydroxytetrahydro-3-furanyl]-2,5,7,8-tetramethyl-3,4dihydro-2H-chromene-2-carboxanmide 1.1) (2R)-6-hydroxy-2,5,7,8-tetramethyl-N-[(3S)-2-oxotetrahydro-3-furanyl]-3,4-dihydro-2H-chromene-2-carboxamide A solution of 1.82 g (7.27 mmoles) of (R)-Trolox and 1.18 g (7.27 mmoles) of 1,1'-carbonyldiimidazole (CDI) in 15 ml of anhydrous THF is stirred for 1 hour at 23° C., before adding a solution of 1 g (7.27 mmoles) of (S)-2-amino4-butyrolactone hydrochloride and 1.27 ml (7.27 mmoles) of N,N-diisopropylethylamine (DIEA) in 15 ml of anhydrous DMF. The reaction mixture is stirred for 15 hours at 23° C. and finally concentrated to dryness under vacuum. The residue is dissolved in 100 ml of AcOEt and the organic solution is washed successively with 50 ml of 1N aqueous HCl, 50 ml of $H_2O$, 50 ml of a saturated aqueous solution of $NaHCO_3$, 50 ml of $H_2O$ and finally 50 ml of salt water. After drying over $MgSO_4$, the organic solution is filtered and concentrated to dryness under vacuum. The residue is taken up in 50 ml of $Et_2O$, followed by agitating and filtering. After rinsing with 2×25 ml of $Et_2O$, the white powder, obtained is dried under vacuum. Melting point: 195–196° C.

1.2) (2R)-6-hydroxy-N-[(3S)-2-hydroxytetrahydro-3-furanyl]-2,5,7,8-tetramethyl-3,4-dihydro-2H-chromene-2-carboxamide 1.53 g (4.59 mmoles) of intermediate 1.1 in 75 ml of anhydrous THF is dissolved in a three-necked flask, under an argon atmosphere. The mixture is cooled down to −78° C., before the introduction, dropwise, using an addition phial, of 18.4 ml (18.4 mmoles) of a 1M solution of DIBAL in $CH_2Cl_2$. After stirring for 3 hours at −78° C.; the reaction is stopped by the slow introduction of 10 ml of MeOH. Once it has risen to 20° C., the reaction mixture is poured into 150 ml of a Rochelle salt solution under vigorous stirring. Stirring is maintained until two phases appear. The mixture is decanted and the aqueous phase is reextracted twice with 50 ml of $CH_2Cl_2$. The organic phases are collected and washed successively with 50 ml of $H_2O$ and 50 ml of salt water. After drying over $MgSO_4$ and filtration, the solvent is evaporated off under vacuum and the residue is purified on a silica column (eluent: Heptane/AcOEt: 2/8). A white powder is obtained. Melting point 67–70° C.

Examples 2 to 11 illustrate compounds capable of being prepared according to the synthesis diagrams described previously.

EXAMPLE 2

2-[(3,5-di(tert-butyl)-4-hydroxyphenyl)sulphanyl]-N-(2-hydroxytetrahydro-3-furanyl)acetamide

EXAMPLE 3

N-1-(2-hydroxytetrahydro-3-furanyl)-N-4-(1-methyl-2,3-dihydro-1H-indol-5-yl)succinamide

EXAMPLE 4

N-1-(4-anilinophenyl)-N-3-(2-hydroxytetrahydro-3-furanyl)-2-isopropylmalonamide

EXAMPLE 5

N-1-(4-anilinophenyl)-N-3-(2-hydroxytetrahydro-3-furanyl)isophthalamide

EXAMPLE 6

N-1-(4-anilinophenyl)-N-4-(2-hydroxytetrahydro-3-furanyl)terephthalamide

EXAMPLE 7

N-1-(4-anilinophenyl)-N-2-(2-hydroxytetrahydro-3-furanyl)phthalamide

EXAMPLE 8

N-{1-[(4-benzyl-5-hydroxy-1,3-oxazolidin-3-yl)carbonyl]-2-methylpropyl}-6-hydroxy-2,5,7,8-tetramethyl-2-chromanecarboxamide

EXAMPLE 9

N-(4-anilinophenyl)-N'-{1-[(4-benzyl-5-hydroxy-1,3-oxazolidin-3-yl)carbonyl]-2-methylpropyl}urea

EXAMPLE 10

N-{1-[(4-benzyl-5-oxo-1,3-oxazolidin-3-yl)carbonyl]-2-methylpropyl}-2-[3,5-di(tert-butyl)-4-hydroxyphenoxy]acetamide

EXAMPLE 11

6-hydroxy-2,5,7,8-tetramethyl-N-{2-methyl-1-[(3-oxo-1-pyrrolidinyl)carbonyl]propyl}-2-chromanecarboxamide

EXAMPLE 12

N-1-(4-anilinophenyl)-N-4-[(3S)-2-hydroxytetrahydro-3-furanyl]succinamide 12.1) 4-(4-anilinoanilino)-4-oxobutanoic Acid The experimental protocol used is the same as that described in J. Amer. Chem. Soc. (1951) 73, 4007, starting from $N^1$-phenyl-1,4-benzenediamine and succinic anhydride in order to produce a pale grey-blue powder. Melting point: 175–176° C.

12.2) N-1-(4-anilinophenyl)-N-4-[(3S)-2-oxotetrahydro3-furanyl]succinamide 4-(4-anilinoanilino)-4-oxobutanoic acid (1.14 g, 4 mmoles) is condensed with (S)-2-amino-4-butyrolactone hydrochloride (0.5 g, 3.6 mmoles) in the presence of 0.54 g (4 mmoles) of HOBT, 1.53 g (8 mmoles) of EDC and 1.66 ml (11.9 mmoles) of triethylamine in 25 ml of dry DMF. The mixture is stirred for 15 hours before concentration to dryness under vacuum. The evaporation residue is divided between 100 ml of AcOEt and 100 ml of a 1M aqueous solution of HCl. A precipitate appears which is filtered on frit and rinsed successively with $H_2O$, AcOEt, $Et_2O$ and $CH_2Cl_2$. 1.12 g of a light grey powder is obtained. Melting point: 202–203° C.

12.3) N-1-(4-anilinophenyl)-N-4-[(3S)-2-hydroxytetrahydro-3-furanyl]succinamide

The experimental protocol used is identical to that described for intermediate 1.2. White powder. Melting point: 178–179° C.

EXAMPLE 13

(3S)-3-{[4-(4-anilinoanilino)-4-oxobutanoyl]amino}tetrahydro-2-furanyl acetate

Intermediate 12.3 (0.15 g, 0.4 mmole) is dissolved in 4 ml of acetic anhydride in the presence of 10 mg (0.08 mmole) of N,N-dimethyl-4-pyridinamine. The reaction mixture is stirred for 3 hours at 20° C. The mixture is finally poured into 25 ml of ice-cold water and extraction is carried out twice using 25 ml of AcOEt. The organic solution is washed successively with 20 ml of a 2M solution of citric acid, 20 ml of $H_2O$, 20 ml of a saturated solution of $NaHCO_3$ and finally 20 ml of salt water. After drying over sodium sulphate, filtration and evaporation of the solvent, the residue is purified on a silica column (eluent: AcOEt). White powder. Melting point: 191–192° C.

EXAMPLE 14

N-1-(4-anilinophenyl)-N-4-[(1S)-1-(1,3-dioxolan-2-yl)-3-methylbutyl]succinamide 14.1) methyl (2S)-2-{[4-(4-anilinoanilino)-4-oxobutanoyl]amino}-4-methylpentanoate The experimental protocol used is identical to that described for intermediate 12.2, with the methyl ester of L-Leucine replacing the (S)-2-amino-4-butyrolactone. Grey powder. Melting point: 134–135° C.

14.2) $N^1$-(4-anilinophenyl)-$N^4$-[(1S)-1-formyl-3-methylbutyl]succinamide

The experimental protocol used is identical to that described for intermediate 1.2 starting from intermediate 14.1. White powder. Melting point: 128–129° C.

14.3) N-1-(4-anilinophenyl)-N-4-[(1S)-1-(1,3-dioxolan-2-yl)-3-methylbutyl]succinamide A mixture of 0.38 g (1 mmole) of intermediate 14.2, 0.06 ml (1.1 mmole) of ethylene glycol and 20 mg of para-toluenesulfonic acid in 30 ml of toluene is heated under reflux for 3 hours. After returning to 20° C., the mixture is diluted with 20 ml of AcOEt and this organic solution is washed with $H_2O$ followed by salt water. After drying over magnesium sulphate, filtration and concentration to dryness under vacuum, the residue is purified on a silica column (eluent: Heptane/AcOEt: 1/9). Cream powder. Melting point: 156–157° C.

EXAMPLE 15

N-1-(4-anilinophenyl)-N-3-[(3S)-2-hydroxytetrahydro-3-furanyl]-2-phenylmalonamide 15.1) Benzyl 3-(4-anilinoanilino)-3-oxo-2-phenylpropanoate The experimental protocol used is the same as that described for intermediate 12.2, starting from N$^1$-phenyl-1,4-benzenediamine and 3-(benzyloxy)-3-oxo-2-phenylpropanoic acid.

15.2) 3-(4-anilinoanilino)-3-oxo-2-phenylpropanoic Acid

Intermediate 15.1 (1.4 g, 3.2 mmoles), dissolved in 30 ml of a CH$_2$Cl$_2$/EtOH mixture 2/1, is placed under a hydrogen atmosphere (1.5 bar) for 1 hour in the presence of 100 mg of 10% Pd/C. After elimination of the Pd/C by filtration, the filtrate is concentrated under vacuum and purified on a silica column (eluent: Heptane/AcOEt: 1/1 to 0/1). Partially crystallized oil.

15.3) N-1-(4-anilinophenyl)-N-3-[(3S)-2-hydroxytetrahydro-3-furanyl]-2-phenylmalonamide The preparation of this compound is carried out in two stages, starting from intermediate 15.2, according to the experimental protocols described for the successive synthesis of intermediates 12.2 and 12.3. Light beige powder. Melting point: 86–86.5° C.

EXAMPLE 16

3-(4-anilinoanilino)tetrahydro-2-furanol 16.1) 3-(4-anilinoanilino)dihydro-2(3H)-furanone A mixture of 1.84 g (10 mmoles) of N$^1$-phenyl-1,4-benzenediamine and 0.41 ml (5 mmoles) of α-bromo-γ-butyrolactone in 20 ml of acetonitrile is heated under reflux for 5 hours. After returning to 20° C., the precipitate which appears during the reaction (N$^1$-phenyl-1,4-benzenediamine hydrobromide) is filtered and rinsed with 20 ml of acetonitrile. The filtrate is concentrated to dryness under vacuum and the residue is purified on a silica column (eluent: Heptane/AcOEt: 1/1 to 4/6). Beige powder. Melting point: 142.5–143° C.

16.2) 3-(4-anilinoanilino)tetrahydro-2-furanol

The experimental protocol used is the same as that described for intermediate 1.2, starting from intermediate 16.1. Off-white powder. Melting point: 139–139.40° C.

EXAMPLE 17

N-[(1S)-1-({[(3S)-2-hydroxytetrahydro-3-furanyl]amino}carbonyl)-3-methylbutyl]-10H-phenothiazine-2-carboxamide 17.1) methyl (2S)-4-methyl-2-[(10H-phenothiazin-2-ylcarbonyl)amino]pentanoate 4.6 ml (33 mmoles) of triethylamine is added to a solution of 1.82 g (10 mmoles) of L-Leucine methyl ester hydrochloride, 2.43 g (10 mmoles) of 10H-phenothiazine-2-carboxylic acid (J. Med. Chem.(1998) 41 (2), 148–156), 1.48 g (11 mmoles) of HOBT and 4.21 g (22 mmoles) of EDC in 30 ml of anhydrous DMF. The reaction mixture is stirred for 15 hours. After evaporation of the solvent under vacuum, the residue is divided between 100 ml of AcOEt and 50 ml of a 1M solution of HCl. The organic phase is decanted and washed successively with 50 ml of H$_2$O, 50 ml of a saturated solution of NaHCO$_3$ and 50 ml of salt water. The organic solution is dried over magnesium sulphate, filtered and concentrated to dryness under vacuum. The evaporation residue is taken up in Et$_2$O and filtered. Yellow powder (71%). Melting point: 160.5–161° C.

17.2) (2S)-4-methyl-2-[(10H-phenothiazin-2-ylcarbonyl)amino]pentanoic acid

A solution of 0.44 g (11 mmoles) of LiOH, H$_2$O in 20 ml of H$_2$O is added in one go to a solution of 1.85 g (5 mmoles) of intermediate 17.1 in 20 ml of THF. The reaction mixture is stirred for 1 hour 30 minutes at 20° C. The mixture is cooled down using an ice bath before the addition of a concentrated aqueous solution of HCl until an acid pH is obtained. After dilution with 100 ml of AcOEt and stirring, the organic phase is decanted.

This is then washed with 20 ml of a 1M aqueous solution of HCl followed by 20 ml of salt water. The organic solution is dried over sodium sulphate, filtered and concentrated to dryness under vacuum. Yellow-green powder. The product is used as it is in the following stage.

17.3) N-[(1S)-3-methyl-1-({[(3S)-2-oxotetrahydro-3-furanyl]amino}carbonyl)butyl]-10H-phenothiazine-2-carboxamide The experimental protocol used is the same as that described for intermediate 12.2, with intermediate 17.2 replacing intermediate 12.1. Yellow powder. Melting point: 151–152° C.

17.4) N-[(1S)-1-({[(3S)-2-hydroxytetrahydro-3-furanyl]amino}carbonyl)-3-methyl butyl]-10H-phenothiazine-2-carboxamide The experimental protocol used is the same as that described for intermediate 1.2, with intermediate 17.3 replacing intermediate 1.1. Yellow powder. Melting point: 100–101° C.

EXAMPLE 18

(3S)-3-({(2S)-4-methyl-2-[(10H-phenothiazin-2-ylcarbonyl)-amino]pentanoyl}amino)tetrahydro-2-furanyl acetate The experimental protocol used is the same as that described for Example 13, starting from intermediate 17.4. The two diastereoisomers 18.1 and 18.2 ,are separated by chromatography on a silica column (eluent: Heptane/AcOEt: 1/1).

18.1) (2R,3S)-3-({(2S)-4-methyl-2-[(10H-phenothiazin-2-ylcarbonyl)amino]-pentanoyl}amino)tetrahydro-2-furanyl acetate Pale yellow powder. Melting point: 199–201° C.

18.2) (2S,3S)-3-({(2S)-4-methyl-2-[(10H-phenothiazin-2-ylcarbonyl)amino]-pentanoyl}amino)tetrahydro-2-furanyl acetate Pale yellow powder. Melting point: 205–208° C.

EXAMPLE 19

N-[(3S)-2-hydroxytetrahydro-3-furanyl]-2-(10H-phenothiazin-2-yl)-1,3-thiazol-4-carboxamide 19.1) 10H-phenothiazine-2-carbothioamide A reaction mixture comprising 3.4 g (14 mmoles) of 10H-phenothiazine-2-carboxamide (J. Org. Chem. (1961) 26, 1138–1143) and 3.4 g (8.4 mmoles) of Lawesson's reagent in solution in 40 ml of 1,4-dioxane to which 20 ml of pyridine is added is heated at 110° C. for 1 hour 30 minutes. The brown solution is then concentrated under vacuum and the residue is diluted in 200 ml of AcOEt and 100 ml of H$_2$O. After stirring and decanting, the organic phase is washed successively with 100 ml of a 1N aqueous solution of HCl and 100 ml of salt water. After drying over sodium sulphate, filtration and evaporation of the solvent under vacuum, an orange powder is obtained. This powder is washed with Et$_2$O, the filtrate is eliminated, and extraction is carried out with acetone. The acetonic filtrate is then concentrated under vacuum and the evaporation residue is then purified on a silica column (eluent: Heptane/AcOEt: 1/1 to 4/6). Orange powder. Melting point: 208–209° C.

19.2) ethyl 2-(10H-phenothiazin-2-yl)-1,3-thiazol-4-carboxylate 2.09 ml (16.5 mmoles) of ethyl bromopyruvate is added to a suspension of 1.43 g (5.53 mmoles) of intermediate 19.1 in 70 ml of absolute EtOH. The reaction mixture is then heated under reflux for 1 hour 30 minutes. After concentration to dryness under vacuum, the black residue obtained is washed with Et$_2$O before being placed at the top of a chromatography column (eluent: Heptane/AcOEt/THF: 6/4/0 to pure THF). Yellow powder (83%).

19.3) 2-(10H-phenothiazin-2-yl)-1,3-thiazol-4-carboxylic acid

A solution of intermediate 19.2 (1.62 g, 4.57 mmoles) in 50 ml of THF is cooled down to 0° C. before the addition in one portion of a solution of 300 mg (7.3 mmoles) of NaOH in 30 ml H$_2$O. Stirring is continued for 15 hours at 20° C. before the reaction mixture is acidified, at 0° C., with an aqueous solution of concentrated HCl. The product is then extracted using 100 ml of AcOEt and the organic solution is washed with 25 ml of H$_2$O followed by salt water. After drying over sodium sulphate, filtration and concentration under vacuum, the residue is purified on a silica column (eluent CH$_2$Cl$_2$/MeOH: 8/2 to 1/1). Yellow powder.

19.4) N-[(3S)-2-oxotetrahydro-3-furanyl]-2-(10H-phenothiazin-2-yl)-1,3-thiazol-4-carboxamide The experimental protocol used is the same as that described for intermediate 12.2, with intermediate 19.3 replacing intermediate 12.1. Yellow powder. Melting point: 277–277.5° C.

19.5) N-[(3S)-2-hydroxytetrahydro-3-furanyl]-2-(10H-phenothiazin-2-yl)-1,3-thiazol-4-carboxamide The experimental protocol used is the same as that described for intermediate 1.2, with intermediate 19.4 replacing intermediate 1.1. Yellow powder. Melting point: 189–190° C.

EXAMPLE 20

N-[4-({[(3S)-2-hydroxytetrahydro-3-furanyl]amino}carbonyl)phenyl]-10H-phenothiazine-2-carboxamide 20.1) 4-[(10H-phenothiazin-2-ylcarbonyl)amino]benzoic acid The experimental protocol used is the same as that described for the syntheses of intermediates 17.1 and 17.2, with methyl 4-aminobenzoate acid replacing L-Leucine methyl ester.

20.2) N-[4-({[(3S)-2-oxotetrahydro-3-furanyl]amino}carbonyl)phenyl]-10H-phenothiazine-2-carboxamide The experimental protocol used is the same as that described for the synthesis of intermediate 12.2, with intermediate 20.1 replacing the 4-(4-anilinoanilino)-4-oxobutanoic acid. Yellow-green powder. Melting point: 284–285° C.

20.3) N-[4-({[(3S)-2-hydroxytetrahydro-3-furanyl]amino}carbonyl)phenyl]-10H-phenothiazine-2-carboxamide The experimental protocol used is the same as that described for intermediate 1.2, with intermediate 20.2 replacing intermediate 1.1. Dark yellow powder. Melting point: 234–235° C.

EXAMPLE 21

N-[(1S)-1-({[(3S)-2-hydroxytetrahydro-3-furanyl]amino}carbonyl)-3-methylbutyl]-10H-phenothiazine-1-carboxamide The experimental protocol used is identical to that described for compound 17, with 10H-phenothiazine-1-carboxylic acid replacing 10H-phenothiazine-2-carboxylic acid. Yellow powder. Melting point: 99–101 ° C.

EXAMPLE 22

(3S)-3-({(2S)-4-methyl-2-[(10H-phenothiazin-2-ylcarbonyl)amino]pentanoyl}amino)tetrahydro-2-furanyl pivalate 0.14 ml of 2,2-dimethylpropanoyl chloride is added dropwise to a solution of 0.45 g (1.02 mmole) of intermediate 17.4 and 0.28 ml (2.04 mmoles) of Et$_3$N in 20 ml of CH$_2$Cl$_2$ cooled down to 0° C. The reaction mixture is then stirred for 24 hours at 22° C. After dilution with 50 ml of CH$_2$Cl$_2$, the organic solution is washed with 20 ml of water followed by 20 ml of salt water, dried over MgSO$_4$, filtered and concentrated to dryness under vacuum. The product is finally purified by chromatography on a silica column (eluent: Heptane/AcOEt: 1/1). Pale yellow solid. Melting point: 107–109° C.

EXAMPLE 23

(3S)-3-({(2S)-4-methyl-2-[(10H-phenothiazin-2-ylcarbonyl)amino]pentanoyl}amino)tetrahydro-2-furanyl 3,3-dimethylbutanoate The experimental protocol used is the same as that described for Example 22, starting from intermediate 17.4 and 3,3-dimethylbutanoyl chloride. Yellow solid. Melting point: 111–113° C.

EXAMPLE 24

(3S)-3-({(2S)-4-methyl-2-[(10H-phenothiazin-2-ylcarbonyl)amino]pentanoyl}amino)tetrahydro-2-furanyl benzoate The experimental protocol used is the same as that described for Example 22, starting from intermediate 17.4 and benzoyl chloride. Pale yellow solid. Melting point: 193–195° C.

EXAMPLE 25

(3S)-3-({(2S)-4-methyl-2-[(10H-phenothiazin-2-ylcarbonyl)amino]pentanoyl}amino)tetrahydro-2-furanyl phenylacetate The experimental protocol used is the same as that described for Example 22, starting from intermediate 17.4 and phenylacetyl chloride. Yellow solid. LC-MS: MH$^+$= 560.2.

EXAMPLE 26

(3S)-3-({(2S)-4-methyl-2-[(10H-phenothiazin-2-ylcarbonyl)amino]pentanoyl}amino)tetrahydro-2-furanyl (2S)-2-(dimethylamino)-3-phenylpropanoate 0.22 g (1.13 mmole) of (2S)-2-(dimethylamino)-3-phenylpropanoic acid and 0.23 g (1.13 mmole) of 1,3-dicyclohexylcarbodiimide are added to a solution of 0.5 g (1.13 mmole) of intermediate 17.4 in 2 ml of $CH_2Cl_2$. After stirring for 72 hours at 22° C., the precipitate is filtered and washed with 10 ml of $CH_2Cl_2$. The filtrate is then washed with a saturated solution of $NaHCO_3$ (10 ml) followed by 10 ml of water and 10 ml of salt water. The organic solution is dried over $MgSO_4$, filtered and concentrated to dryness. The evaporation residue is purified on a silica column (eluent: AcOEt). Yellow solid. LC-MS: $MH^+$=617.2.

EXAMPLE 27

(3S)-3-({(2S)-4-methyl-2-[(10H-phenothiazin-2-ylcarbonyl)amino]pentanoyl}amino)tetrahydro-2-furanyl 4-morpholinecarboxylate The experimental protocol used is the same as that described for Example 22, starting from intermediate 17.4 and morpholine chloroformate. Yellow solid. Melting point: 165–167° C.

EXAMPLE 28

N-{(1S)-3-methyl-1-[(3-oxo-1-pyrrolidinyl)carbonyl]butyl}-10H-phenothiazine-2-carboxamide 28.1) N-[(1S)-1-(1,4-dioxa-7-azaspiro[4.4]non-7-ylcarbonyl)-3-methylbutyl]-10H-phenothiazine-2-carboxamide 0.23 g (1.76 mmole) of 1,4-dioxa-7-azaspiro[4.4]nonane (J. Med. Chem. (1992) 35 (8), 1392–1398), 0.26 g (1.93 mmole) of HOBT, 0.74 g (3.86 mmoles) of EDC and finally 0.54 ml (3.86 mmoles) of $Et_3N$ are added successively to a solution of 0.62 g (1.76 mmole) of intermediate 17.2 in 30 ml of $CH_2Cl_2$. The reaction mixture is stirred for 15 hours at 22° C. After dilution with 20 ml of water and stirring, the organic phase is decanted and washed successively with 20 ml of water and 20 ml of salt water. The organic solution is finally dried over $MgSO_4$, filtered and concentrated to dryness. The evaporation residue is purified on a silica column (eluent: Heptane/AcOEt: 1/1). Yellow solid. Melting point: 75–77° C.

28.2) N-{(1S)-3-methyl-1-[(3-oxo-1-pyrrolidinyl)carbonyl]butyl}10H-phenothiazine-2-carboxamide A solution of 0.28 g (0.6 mmole) of intermediate 28.1 in 14 ml of $CH_3OH$ and 10 ml of 8% $H_2SO_4$ is heated for 7 hours at 60° C. The reaction mixture is finally diluted with 20 ml of water and 30 ml of AcOEt. After stirring and decanting, the organic phase is washed successively with 20 ml of a 1M solution of $NaHCO_3$ and 20 ml of salt water. The organic solution is finally dried over $Na_2SO_4$, filtered and concentrated to dryness. The evaporation residue is purified on a silica column (eluent Heptane/AcOEt: 1/1). Yellow solid. LC-MS: $MH^+$=424.3.

EXAMPLE 29

2-(3,5-di-tert-butyl-4-hydroxyphenoxy)-N-[(3S)-2-hydroxytetrahydro-3-furanyl]acetamide 29.1) 2-[3,5-di(tert-butyl)-4-hydroxyphenoxy]acetic acid 3.6 ml (46 mmol) of trifluoroacetic acid is added to a solution of 1.56 g (4.64 mmol) of tert-butyl 2-[3,5-di(tert-butyl)-4-hydroxyphenoxy]acetate (prepared according to J. Heterocycl. Chem. (1994) 31, 1439–1443) in 20 ml of dichloromethane. The reaction mixture is stirred for 1 hour, concentrated under vacuum and the residue is dissolved in 50 ml of $Et_2O$. The organic solution is extracted twice with 25 ml of a saturated solution of $NaHCO_3$, the aqueous phase is then washed with 25 ml of $Et_2O$. The basic aqueous solution is then acidified, at 0° C., with a saturated solution of $KHSO_4$ and finally the expected product is extracted twice using 25 ml of $Et_2O$. The organic solution is dried over sodium sulphate, filtered and concentrated under vacuum in order to produce a yield of 70% of a white powder. Melting point: 172–173 ° C.

29.2) 2-(3,5-di-tert-butyl-4-hydroxyphenoxy)-N-[(3S)-2-oxotetrahydro-3-furanyl]acetamide The experimental protocol used is the same as that described for intermediate 12.2, starting from intermediate 29.1. White solid. Melting point: 162.5–163 ° C.

29.3) 2-(3,5-di-tert-butyl-4-hydroxyphenoxy)-N-[(3S)-2-hydroxytetrahydro-3-furanyl]acetamide The experimental protocol used is the same as that described for intermediate 1.2, starting from intermediate 29.2. White solid. Melting point: 133.5–134° C.

EXAMPLE 30

$N^1$-[(3S)-2-hydroxytetrahydro-3-furanyl]-2-phenyl-$N^3$(1-propyl-2,3-dihydro-1H-indol-5-yl)malonamide 30.1) 5-nitro-1-propylindoline 0.51 g (12.79 mmoles) of 60% NaH is added, at 20° C., by portions, to a solution of 2 g (12.18 mmoles) of 5-nitroindoline in 16 ml of anhydrous DMF. After stirring for a further 30 minutes, 2.32 ml (25.58 mmoles) of 1-bromopropane is added dropwise. Stirring is maintained overnight and the reaction mixture is finally diluted with 50 ml of water and 50 ml of AcOEt. After stirring and decanting, the organic phase is successively washed with 25 ml of water and 25 ml of salt water, dried over $Na_2SO_4$, filtered and concentrated to dryness under vacuum. The evaporation residue is then purified on a silica column (eluent: Heptane/AcOEt: 9/1). Orange oil.

30.2) 1-propyl-2,3-dihydro-1H-indol-5-ylamine

Approximately 400 mg of Raney nickel is added to a mixture of 3.28 g (15.9 mmol) of 5-nitro-1-propylindoline and 4 ml (80 mmol) of hydrazine hydrate in 60 ml of absolute ethanol. The reaction mixture is heated under reflux for 5 hours. After returning to 23° C., a little silica is added to the flask and the solvent is evaporated off under vacuum. The evaporation residue is placed directly at the top of a chromatography column. The expected product is eluted using a Heptane/AcOEt mixture (1/9). A black oil is obtained which is used directly in the following stage.

30.3) $N^1$-[(3S)-2-hydroxytetrahydro-3-furanyl]-2-phenyl-$N^3$-(1-propyl-2,3-dihydro-1H-indol-5-yl)malonanide The experimental protocol used is the same as that described for Example 15, starting from intermediate 30.2. Yellow solid. LC-MS: $MH^+$=424.2.

EXAMPLE 31

N-(2-anilinophenyl)-N'-[(3S)-2-hydroxytetrahydro-3-furanyl]urea 31.1) N-(2-anilinophenyl)-N'-[(3S)-2-oxotetrahydro-3-furanyl]urea A solution of 1.48 g (8.15 mmoles) of (S)-2-amino-4-butyrolactone hydrobromide and 3.12 ml (17.9 mmoles) of diisopropylethylamine in 80 ml of anhydrous $CH_2Cl_2$ is added slowly (4 hours) into a three-necked flask containing a solution of 0.89 g (3 mmoles) of triphosgene in 45 ml of anhydrous $CH_2Cl_2$, under an inert atmosphere. After stirring for a further 15 minutes, a solution of 1.5 g (8.15 mmoles) of $N^1$-phenyl-1,2-benzenediamine and 3.12 ml (17.9 mmoles) of diisopropylethylamine in 45 ml of anhydrous $CH_2Cl_2$ is added in one go. The reaction mixture is then heated for 5 hours at 60° C. After concentration to dryness under vacuum, the residue is divided between 50 ml of AcOEt and 50 ml of water. After stirring and decanting, the organic phase is washed successively with 50 ml of water and 50 ml of salt water. The organic solution is then dried over $Na_2SO_4$, filtered and concentrated under vacuum. The evaporation residue is then purified on a silica column (eluent: Heptane/AcOEt: 1/2). Pink solid.
Melting point: 63–65° C.
31.2) N-(2-anilinophenyl)-N'-[(3S)-2-hydroxytetrahydro-3-furanyl]urea The experimental protocol used is the same as that described for intermediate 1.2, starting from intermediate 31.1. Pale pink solid. LC-MS: $MH^+$=314.3.

EXAMPLE 32

$N^1$-[(3S)-2-hydroxytetrahydro-3-furanyl]-$N^2$-(1-propyl-2,3-dihydro-1H-indol-5-yl)ethanediamide The experimental protocol used is the same as that described for Example 30, with ethyl chloro(oxo)acetate being used instead of 3-(benzyloxy)-3-oxo-2-phenylpropanoic acid. Pale yellow solid. Melting point: 120–122° C.

EXAMPLE 33

(2R)-N-[(1S)-1-(1,3-dioxolan-2-yl)-2-phenylethyl]-6-hydroxy-2,5,7,8-tetramethyl-3,4-dihydro-2H-chromene-2-carboxamide The experimental protocol used is the same as that described for Example 14, with (R)-Trolox being used instead of intermediate 12.1 and the methyl ester of L-phenylalanine replacing the L-Leucine methyl ester. Yellow oil. LC-MS: $MH^+$=426.2.

EXAMPLE 34

N-[(3S)-2-hydroxytetrahydro-3-furanyl]-5-indolinecarboxamide 34.1) tert-butyl 5-methyl 1,5-indolinedicarboxylate
1.26 g (5.8 mmoles) of di-tert-butyldicarbonate and 0.80 ml (5.8 mmoles) of $Et_3N$ are added successively at 20° C. to a solution of 0.85 g (4.8 mmoles) of methyl 5-indolinecarboxylate (J Heterocycl Chem (1993) 30 (4), 1133–1136) in 15 ml of $CH_2Cl_2$. The reaction mixture is stirred for 20 hours and concentrated to dryness under vacuum. The residue is divided between 50 ml of AcOEt and 25 ml of water. After stirring and decanting, the organic phase is washed with 25 ml of salt water, dried over $MgSO_4$, filtered and concentrated to dryness under vacuum. The powder obtained is suspended in heptane, stirred and filtered in order to produce a white solid with a yield of 73%. Melting point=107–107.5° C.
34.2) 1-(tert-butoxycarbonyl)-5-indolinecarboxylic acid A solution of 0.97 g (3.49 mmoles) of intermediate 34.1 and of 0.16 g (3.84 mmoles) of LiOH in a mixture of 20 ml of THF and 20 ml of water is stirred for 24 hours, at 20° C. The reaction mixture is then cooled down using an ice bath, acidified using a 1M $KHSO_4$ solution and diluted with 50 ml of AcOEt. The organic phase is then decanted, washed with 25 ml of salt water, dried over $MgSO_4$, filtered and concentrated to dryness under vacuum. A white solid is obtained (92%) which is used as it is in the following stage.
34.3) tert-butyl 5-({[(3S)-2-oxotetrahydro-3-furanyl]amino}carbonyl)-1-indolinecarboxylate The experimental protocol used is the same as that described for intermediate 12.2, with intermediate 34.2 replacing intermediate 12.1. White solid. Melting point: 172.5–173° C.

34.4) tert-butyl 5-({[(3S)-2-hydroxytetrahydro-3-furanyl]amino}carbonyl)-1indolinecarboxylate The experimental protocol used is the same as that described for intermediate 1.2, with intermediate 34.3 replacing intermediate 1.1. White solid. Melting point: 141–141.5° C.
34.5) N-[(3S)-2-hydroxytetrahydro-3-furanyl]-5-indolinecarboxamide 6 ml (24 mmoles) of a 4N solution of HCl in dioxane is added dropwise to a solution of 0.4 g (1.15 mmoles) of intermediate 34.4 in 10 ml of $CH_2Cl_2$, cooled down using an ice bath. After stirring for 2 hours at 20° C., the reaction mixture is concentrated to dryness under vacuum. The residue is dissolved in 20 ml of water and the aqueous solution is washed successively with 20 ml of AcOEt and 20 ml of $CH_2Cl_2$. The aqueous phase is then rendered basic by the addition of a saturated solution of $Na_2CO_3$ and the product is finally extracted twice using 20 ml of AcOEt. The organic solution is dried over $MgSO_4$, filtered and concentrated under vacuum. The evaporation residue is purified on a silica column (eluent: $CH_2Cl_2$/Acetone: 1/1). White solid. LC-MS: $MH^+$=249.2.

Examples 35 to 37 illustrate compounds capable of being prepared according to the synthesis diagrams described previously.

EXAMPLE 35

(2S)-2-{[(4-anilinoanilino)carbonyl]amino}-N-[(3S)-2-hydroxytetrahydro-3-furanyl]-4-methylpentanamide

EXAMPLE 36

(2S)-2-({[(1-benzyl-2,3-dihydro-1H-indol-5-yl)amino]carbonyl}amino)-N-[(3S)-2-hydroxytetrahydro-3-furanyl]-4-methylpentanamide

EXAMPLE 37

(2S)-N-[(3S)-2-hydroxytetrahydro-3-furanyl]-4-methyl-2-[({[1-(1-naphthylmethyl)-2,3-dihydro-1H-indol-5-yl]amino}carbonyl)amino]pentamide Pharmacological Study of the Products of the Invention
Study of the Effects on Porcine Calpain I The method used is that described by Mallya et al. (Biochemical and biophysical research communications 248 293–296 (1998)). The calpain in vitro activity is determined by measuring the fluorescence due to the degradation of an artificial substrate of the Suc-LY-AMC enzyme (Suc-Leu-Tyr-aminomethylcoumarin). The aminomethylcoumarin released fluoresces at 460 nm under excitation at 380 nm. The inhibitors tested are dissolved in DMSO at 40 times the final concentration. 5 µl of solution is deposited in a 96-well plate with black walls. 175 µl/well of reaction buffer containing calpain I and its substrate are then added. The reaction is started by adding 20 µl of $CaCl_2$ 50 mM. The plates are incubated at 25° C. and the fluorescence (380 nm excitation and 460 nm transmission) is read after 30 minutes using a microplate reader (Victor, Wallack). The $IC_{50}$'s are determined by calculating the product fluorescence/DMSO control fluorescence ratio. Composition of the enzymatic reaction buffer: :Tris-HCl 50 mM pH 7.5, NaCl 50 mM, EDTA 1 mM, EGTA 1 mM, b-Mercaptoethanol 5 mM, Suc-LY-AMC 1 mM (Bachem, ref I-1355) and 2.5 U/ml Calpain I (porcine erythrocytes, Calbiochem ref 208712). ). In this test, the $IC_{50}$ value of certain compounds according to the invention is lower than 5µM.

Study of the Effects on Lipidic Peroxidation in the Cerebral Cortex of the Rat

The inhibitory activity of the products of the invention is determined by measuring their effects on the degree of lipidic peroxidation, determined by the concentration of malondialdehyde (MDA). The MDA produced by the peroxidation of unsaturated fatty acids is a good indicator of lipidic peroxidation (H Esterbauer and K H Cheeseman, Meth. Enzymol. (1990) 186: 407–421). Male Sprague Dawley rats weighing 200 to 250 g (Charles River) were sacrificed by decapitation. The cerebral cortex is removed, then homogenised with a Thomas potter in a Tris-HCl buffer, 20 mM, pH=7.4. The homogenate is centrifuged twice at 50,000 g for 10 minutes at 4° C. The pellet is kept at −80° C. On the day of the experiment, the pellet is resuspended at a concentration of 1 g/15 ml and centrifuged at 515 g for 10 minutes at 4° C. The supernatant is used immediately to determine lipidic peroxidation. The homogenate of rat cerebral cortex (500 μl) is incubated at 37° C. for 15 minutes in the presence of the: compounds to be tested or of the solvent (10 μl). The lipidic peroxidation reaction is initiated by adding 50 μl of $FeCl_2$ at 1 mM, EDTA at 1 mM and ascorbic acid at 4 mM. After incubation for 30 minutes at 37° C., the reaction is stopped by adding 50 μl of a solution of di tert butyl toluene hydroxyl (BHT, 0.2%). The MDA is quantified using a colorimetric test, by reacting a chromogenic reagent (R), N-methyl-2-phenylindole (650 μl), with 200 μl of the homogenate for 1 hour at 45° C. Condensation of a molecule of MDA with two molecules of reagent R produces a stable chromophore the maximum absorbance wavelength of which is equal to 586 nm. (Caldwell et al. European J. Pharmacol. (1995) 285, 203–206). In this test, the $IC_{50}$ value of the compounds according to the invention is lower than 5μM.

What is claimed is:

1. A compound of the formula

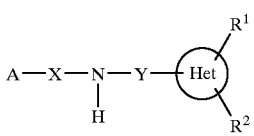

(I)

in racemic, enantiomeric or diastereoisomeric form and all combinations of these forms, wherein $R^1$ is selected from the group consisting of hydrogen, —$OR^3$, —$SR^3$, oxo and cyclic acetal,
  $R^3$ is selected from the group consisting of hydrogen, alkyl, aralalkyl, heterocycloalkylcarbonyl, alkylcarbonyl, arylcarbonyl and aralkylcarbonyl, the akyl, aryl or heterocycloalkyl unsubstituted or substituted by at least one member selected from the group consisting of alkyl, —OH, alkoxy, nitro, cyano, halogen and —$NR^4R^5$;
  $R^4$ and $R^5$ are independently selected from the group consisting of hydrogen or alkyl, or $R^4$ and $R^5$ together with the nitrogen atom to which they are attached form an optionally substituted heterocycle, $R^2$ is selected from the group consisting of hydrogen, alkyl, aryl, and aralkyl, the aryl group being unsubstituted or substituted by at least one member selected from the group consisting of —$OR^6$, —$NR^7R^8$, halogen, cyano, nitro and alkyl,
  $R^6$, $R^7$, and $R^8$ are independently selected from the group consisting of hydrogen, alkyl, aryl, aralkyl, alkylcarbonyl, arylcarbonyl and aralkylcarbonyl, A is

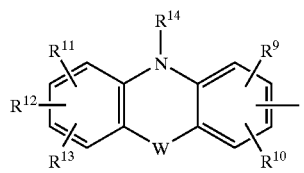

A1 wherein $R^9$, $R^{10}$, $R^{11}$, $R^{12}$, $R^{13}$ are independently selected from the group consisting of hydrogen, halogen, —OH, alkyl, alkoxy, cyano, nitro and —$NR^{15}R^{16}$, $R^{15}$ and $R^{16}$ are independently selected from the group consisting of hydrogen, alkyl and —$COR^{17}$, or $R^{15}$ and $R^{16}$ together with the nitrogen atom to which they are attached form an optionally substituted heterocycle, $R^{17}$ is selected from the group consisting of hydrogen, alkyl, alkoxy and —$NR^{18}R^{19}$, $R^{18}$ and $R^{19}$ are independently selected from the group consisting of hydrogen or alkyl, or $R^{18}$ and $R^{19}$ together with the nitrogen atom to which they are attached form an optionally substituted heterocycle, $R^{14}$ is hydrogen, alkyl and —$COR^{20}$, $R^{20}$ is selected from the group consisting of hydrogen, alkyl, alkoxy, aryl, aralkyl, heterocycloalkyl and —$NR^{21}R^{22}$,
  in which the alkyl, aryl or heterocycloalkyl are unsubstituted or substituted by at least one member selected from the group consisting of alkyl, —OH, alkoxy, nitro, cyano, halogen, and —$NR^4R5$;

$R^{21}$ and $R^{22}$ are independently selected from the group consisting of hydrogen and alkyl, or $R^{21}$ or $R^{22}$ together with the nitrogen atom to which they are attached form an optionally substituted heterocycle, W is S, X is selected from the group consisting of —$(CH_2)_n$—, —$(CH_2)_n$—CO—, —$N(R^{45})$—CO—$(CH_2)_n$—CO—, —$N(R^{45})$—CO—D—CO—, —CO—$N(R^{45})$—D—CO—, —CO—D—CO—, —CH=CH—$(CH_2)_n$—CO—,
—$N(R^{45})$—$(CH_2)_n$—CO—, —$N(R^{45})$—CO—C—$(R^{46}R^{47})$—CO—, —O—$(CH_2)_n$—CO—, —$N(R^{45})$—CO—NH—$C(R^{46}R^{47})$—CO—, —CO—$N(R^{45})$—$C(R^{46}R^{47})$—CO—, —S—$(CH_2)_n$—CO— and —Z—CO—;

D is phenylene unsubstituted or substituted by at least one member of the group consisting of alkyl, alkoxy, —OH, nitro, halogen, cyano, and carboxyl optionally esterified by alkyl;

Z is heterocycle, $R^{45}$ is hydrogen or alkyl, $R^{46}$ and $R^{47}$ are independently selected from the group consisting of the group consisting of hydrogen, alkyl, aryl and aralkyl, the alkyl and aryl groups are unsubstituted or substituted by at least one member selected from the group consisting of —OH, —SH, halogen, nitro, alkyl, alkoxy, alkylthio, aralkoxy, aryl-alkylthio, —$NR^{48}R^{49}$ and carboxyl optionally esterified by alkyl;

$R^{48}$ and $R^{49}$ are independently selected from the group consisting of hydrogen, alkyl, and —$COR^{50}$, $R^{48}$ and $R^{49}$ together with the nitrogen atom to which they are attached form an optionally substituted heterocycle;

$R^{50}$ is hydrogen, alkyl, alkoxy and —$NR^{51}R^{52}$.

$R^{51}$ and $R^{52}$ are independently hydrogen or alkyl, or $R^{51}$ and $R^{52}$ together with the nitrogen atom to which they are attached, form an optionally substituted heterocycle;

n is an integer between 0 and 6;

Y is —$(CH_2)_p$—; P is O;

Het is a heterocycle or a pharmaceutically acceptable addition salt with acids or bases thereof, with the exception of the compounds of formula (I) wherein Het is tetrahydrofuran or tetrahydropyran, $R^1$ is $OR^3$, $R^3$ is selected from the group consisting of hydrogen, alkyl, arylalkyl, heterocycloalkylcarbonyl, the heterocycloalkyl being connected by a carbon atom, alkylcarbonyl, arylcarbonyl or aralkylcarbonyl, $R^2$ is hydrogen and Y is —$(CH_2)_p$— with p=0, the X is —CO—N($R^{45}$)—C—($R^{46}R^{47}$)—CO— with $R^{45}$=$R^{46}$=H and with the exclusion of the compound wherein i) X represents —$CH_2$—C(O)— and Het 4-oxo-4H-1-benzopyran-2-yl;

ii) X represents —NH—C(O)—C(O)— and Het phenothiazin-1-yl;

iii) X represents —$CH_2$— and Het 1-azabicyclo[2.2.2]oct-3yl.

2. A compound of claim 1 wherein Het is a monocyclic of 1 to 2 heteroatoms selected from the group consisting of O and N.

3. A compound of claim 1 wherein Het is tetrahydrofuran, dioxolane, pyrrolidine and 1,3-oxazolidine, and $R^1$ is selected from the group consisting of hydrogen, —$OR^3$ and oxo.

4. A compound of claim 1 wherein X is selected from the group consisting of —$(CH_2)_n$—, —$(CH_2)_n$—CO—, —O—$(CH_2)_n$—CO—, —CO—N($R^{45}$)—D—CO—, —N($R^{45}$)—CO—$(CH_2)_n$—CO—, —N($R^{45}$)—CO—C($R^{46}R^{47}$)—CO—, —N($R^{45}$)—CO—NH—C($R^{46}R^{47}$)—CO—, —N($R^{45}$)—$(CH_2)_n$—CO—, —CO—N($R^{45}$)—C($R^{46}R^{47}$)—CO— and —Z—CO.

5. A compound of claim 4 wherein $R^{45}$ and $R^{47}$ are hydrogen, $R^{46}$ is selected from the group consisting of hydrogen, alkyl or phenyl, D is selected from the group consisting of phenylene and Z is thiazole.

6. A compound of claim 1 wherein $R^2$ is hydrogen or aralkyl.

7. A compound selected from the group consisting of

N-[(1S)-1-({[(3S)-2-hydroxytetrahydro-3-furanyl]amino}carbonyl)-3-methylbutyl]-10H-phenothiazine-2-carboxamide;

(3S)-3-({(2S)-4-methyl-2-[(10H-phenothiazin-2-ylcarbonyl)-amino]pentanoyl}amino)tetrahydro-2-furanyl acetate;

N-[(3S)-2-hydroxytetrahydro-3-furanyl]-2-(10H-phenothiazin-2-yl)-1,3-thiazol-4-carboxamide;

N-[4-({[(3S)-2-hydroxytetrahydro-3-furanyl]amino}carbonyl)phenyl]-10H-phenothiazine-2-carboxamide;

N-[(1S)-1-({[(3S)-2-hydroxytetrahydro-3-furanyl]amino}carbonyl)-3-methylbutyl]-10H-phenothiazine-1-carboxamide;

(3S)-3-({(2S)-4-methyl-2-[(10H-phenothiazin-2-ylcarbonyl)amino]pentanoyl}amino)tetrahydro-2-furanyl pivalate;

(3S)-3-({(2S)-4-methyl-2-[(10H-phenothiazin-2-ylcarbonyl)amino]pentanoyl}amino)-tetrahydro-2-furanyl3,3-dimethylbutanoate;

(3S)-3-({(2S)-4-methyl-2-[(10H-phenothiazin-2-ylcarbonyl)amino]pentanoyl}amino) tetrahydro-2-furanyl benzoate;

(3S)-3-({(2S)-4-methyl-2-[(10H-phenothiazin-2-ylcarbonyl)amino]pentanoyl}amino) tetrahydro-2-furanyl phenylacetate;

(3S)-3-({(2S)-4-methyl-2-[(10H-phenothiazin-2-ylcarbonyl)amino]pentanoyl}amino) tetrahydro-2-furanyl(2S)-2-(dimethylamino)-3-phenylpropanoate; and (3S)-3-({(2S)-4-methyl-2-[(10H-phenothiazin-2-ylcarbonyl)amino]pentanoyl}amino) tetrahydro-2-furanyl 4-morpholinecarboxylate.

8. A compound selected from the group consisting of methyl (2S)-4-methyl-2-[(10H-phenothiazin-2-ylcarbonyl)amino]pentanoate;

(2S)-4-methyl-2-[(10H-phenothiazin-2-ylcarbonyl)amino]pentanoic acid;

N-[(1S)-3-methyl-1-({[(3S)-2-oxotetrahydro-3-furanyl]amino}carbonyl)butyl]-10-phenothiazine-2-carboxamide;

ethyl 2-(10H-phenothiazin-2-yl)-1,3-thiazol-4-carboxylate;

2-(10H-phenothiazin-2-yl)-1,3-thiazol-4-carboxylic acid;

N-[(3S)-2-oxotetrahydro-3-furanyl]-2-(10H-phenothiazin-2-yl)-1,3-thiazol-4-carboxamide;

methyl 4-[(10H-phenothiazin-2-ylcarbonyl)amino]benzoate;

4-[(10H-phenothiazin-2-ylcarbonyl)amino]benzoic acid;

N-[4-({[(3S)-2-oxotetrahydro-3-furanyl]amino}carbonyl)phenyl]-10H-phenothiazine-2-carboxamide;

methyl (2S)-4-methyl-2-[(10H-phenothiazin-1-ylcarbonyl)amino]pentanoate;

(2S)-4-methyl-2-[(10H-phenothiazin-1-ylcarbonyl)amino]pentanoic acid;

N-[(1S)-1-({[(3S)-2-oxotetrahydro-3-furanyl]amino}carbonyl)-3-methylbutyl]-10H-phenothiazine-carboxamide; and N-[(1S)-1-(1,4-dioxa-7-azaspiro[4.4]non-7-ylcarbonyl)-3-methylbutyl]-10H-phenothiazine-2-carboxamide.

9. A pharmaceutical composition for inhibition of calpains and/or reactive oxygen species comprising a calpain inhibiting or reactive oxygen species amount of a species of a compound of claim 1 and a pharmaceutical carrier.

10. A method of inhibiting calpain and/or reactive oxygen species in warm-blooded animals comprising administering to warm-blooded animals in need thereof a calpain inhibiting and/or reactive oxygen species inhibiting amount of a compound of the formula

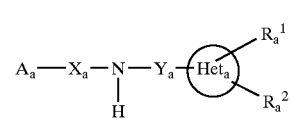

(I_a)

in racemic, enantiomeric, diastereoisomeric form or all combinations of these forms, wherein $R^1$ is hydrogen, —$OR^3$, —$SR^3$, oxo and cyclic acetal, $R^3$ is hydrogen, alkyl, arylalkyl, heterocycloalkylcarbonyl, alkylcarbonyl, arylcarbonyl and aralkylcarbonyl, in which the alkyl, aryl or heterocycloalkyl are unsubstituted or substituted by at least one member selected from the group consisting of alkyl, —OH, alkoxy, nitro, cyano, halogen and —$NR^4R^5$;

$R^4$ and $R^5$ are independently hydrogen or alkyl, or $R^4$ and $R^5$ together with the nitrogen atom to which they are attached form an optionally substituted heterocycle, $R_a^2$ is hydrogen, alkyl, aryl and aralkyl, the aryl being unsubstituted or substituted by at least one member selected from the group consisting of —OR$^6$, —NR$^7$R$^8$, halogen, cyano, nitro and alkyl, R$^6$, R$^7$ and R$^8$ are independently hydrogen, alkyl, aryl, aralkyl, alkylcabonyl, arylcarbonyl and aralkylcarbonyl;

A$_a$ is

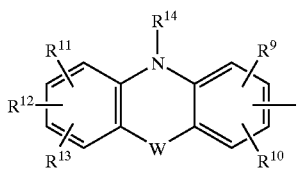

A1 wherein R$^9$, R$^{10}$, R$^{11}$, R$^{12}$, R$^{13}$ are independently selected from the group consisting of hydrogen, halogen, —OH, alkyl, alkoxy, cyano, nitro and —NR$^{15}$R$^{16}$, R$^{15}$ and R$^{16}$ are independently selected from the group consisting of hydrogen, alkyl and —COR$^{17}$, or R$^{15}$ and R$^{16}$ together with the nitrogen atom to which they are attached form an optionally substituted heterocycle, R$^{17}$ is selected from the group consisting of hydrogen, alkyl, alkoxy and —NR$^{18}$R$^{19}$, R$^{18}$ and R$^{19}$ are independently hydrogen or alkyl, or R$^{18}$ and R$^{19}$ together with the nitrogen atom to which they are attached form an optionally substituted heterocycle, R$^{14}$ is hydrogen or alkyl or —COR$^{20}$, R$^{20}$ is hydrogen, alkyl, alkoxy, aryl, aralkyl, heterocycloalkyl and —NR$^{21}$R$^{12}$, the alkyl, aryl or heterocycloalkyl are unsubstituted or substituted by at least one member selected from the group consisting of alkyl, OH, alkoxy, nitro, cyano, halogen and —NR$^4$R$^5$;

R$^{21}$ and R$^{22}$ are independently hydrogen or alkyl, or R$^{21}$ and R$^{22}$ together with the nitrogen atom to which they are attached form an optionally substituted heterocycle, W is S;

X$_a$ is —(CH$_2$)$_n$—, —(CH$_2$)$_n$—CO—, —N(R$^{45}$)—CO—(CH$_2$)$_n$—CO—, —N(R$^{45}$)—CO—D—CO—, —CO—N(R$^{45}$)—D—CO—, —CO—D—CO—, —CH=CH—(CH$_2$)$_n$—CO—, —N(R$^{45}$)—(CH$_2$)$_n$—CO—, —N(R$^{45}$)—CO—C(R$^{46}$R$^{47}$)—CO—, —O—(CH$_2$)$_n$—CO—, —N(R$^{45}$)—CO—NH—C(R$^{46}$R$^{47}$)—CO—,—CO—N(R$^{45}$)—C(R$^{46}$R$^{47}$)—CO—,—S—(CH$_2$)$_n$—CO— and —Z—CO—;

D is phenylene unsubstituted or substituted by at least one member selected from the group consisting of alkyl, alkoxy, —OH, nitro, halogen, cyano and carboxyl optionally esterified by an alkyl radical;

Z is a heterocycle,

R$^{45}$ is hydrogen or alkyl;

R$^{46}$ and R$^{47}$ are independently selected from the group consisting of hydrogen, alkyl, aryl and aralkyl, the alkyl and aryl groups are unsubstituted or substituted by at least one member of the group consisting of —OH —SH, halogen, nitro, alkyl, alkoxy, alkylthio, aralkoxy, aryl-alkylthio, —NR$^{48}$R$^{49}$ and carboxyl optionally esterified by alkyl;

R$^{48}$ and R$^{49}$ are independently selected from the group consisting of hydrogen, alkyl and —COR$^{50}$, or R$^{48}$ and R$^{49}$ together with the nitrogen atom to which they are attached form an optionally substituted heterocycle, R$^{50}$ is selected from the group consisting of hydrogen, alkyl, alkoxy and —NR$^{51}$R$^{52}$, R$^{51}$ and R$^{52}$ are independently selected from the group consisting of hydrogen or alkyl, or R$^{51}$ and R$^{52}$ together with the nitrogen atom to which they are attached form an optionally substituted heterocycle;

n is an integer between 0 and 6;

Y$_a$—(CH$_2$)$_p$—; P is O;

Het$_a$ is a heterocycle, and pharmaceutically acceptable addition salts thereof with acids or bases.

11. The method of claim 10 wherein Het is a monocyclic containing 1 to 2 heteroatoms of O or N.

12. The method of claim 10 wherein Het is selected from the group consisting of tetrahydrofuran, dioxolane, pyrrolidine and 1,3-oxazolidine, and R$^1$ is selected from the group consisting of hydrogen, —OR$^3$ and oxo.

13. The method of claim 10 wherein X is selected from the group consisting of —(CH$_2$)$_n$—, —(CH$_2$)$_n$—CO—, —O—(CH$_2$)$_n$—CO, —CO—N(R$^{45}$)—D—CO—, —N(R$^{45}$)—CO—(CH$_2$)$_n$—CO—, —N(R$^{45}$)—CO—C(R$^{46}$R$^{47}$)—CO—, —N(R$^{45}$)—CO—NH—C (R$^{46}$R$^{47}$)—CO—, —N(R$^{45}$)—(CH$_2$)$_n$—CO—, —CO—N(R$^{45}$)—C(R$^{46}$R$^{47}$)—CO and —Z—CO—.

14. The method of claim 10 wherein R$^{45}$ and R$^{47}$are hydrogen, R$^{46}$ is hydrogen, alkyl and phenyl, D is phenylene and Z is thiazole.

15. The method of claim 10 wherein R$^2$ is hydrogen or aralkyl.

16. The method of claim 10 wherein the inhibitor is that of a reactive oxygen species.

17. The method of claim 10 wherein the inhibitor is that of calpain and a reactive oxygen species.

* * * * *